(12) United States Patent
Zang

(10) Patent No.: US 11,261,253 B2
(45) Date of Patent: **\*Mar. 1, 2022**

(54) HHLA2 AS A NOVEL INHIBITOR OF HUMAN IMMUNE SYSTEM AND USES THEREOF

(71) Applicant: ALBERT EINSTEIN COLLEGE OF MEDICINE, Bronx, NY (US)

(72) Inventor: Xingxing Zang, New York, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 95 days.

This patent is subject to a terminal disclaimer.

(21) Appl. No.: 16/121,771

(22) Filed: Sep. 5, 2018

(65) Prior Publication Data

US 2019/0010234 A1   Jan. 10, 2019

Related U.S. Application Data

(63) Continuation of application No. 14/770,120, filed as application No. PCT/US2014/015308 on Feb. 7, 2014, now Pat. No. 10,093,737.

(60) Provisional application No. 61/771,305, filed on Mar. 1, 2013.

(51) Int. Cl.
*C07K 16/28*     (2006.01)

(52) U.S. Cl.
CPC ...... *C07K 16/2827* (2013.01); *C07K 2317/21* (2013.01); *C07K 2317/24* (2013.01); *C07K 2319/30* (2013.01)

(58) Field of Classification Search
CPC ............ C07K 16/2827; C07K 2317/21; C07K 2317/24; C07K 2319/30
USPC ..................................................... 424/133.1
See application file for complete search history.

(56) References Cited

U.S. PATENT DOCUMENTS

| | | | |
|---|---|---|---|
| 686,339 A | 11/1901 | Ritchie | |
| 2,696,852 A | 12/1954 | Dunton | |
| 2,839,100 A | 6/1958 | Valicenti | |
| 2,985,202 A | 5/1961 | Wilson | |
| 4,370,909 A | 2/1983 | Jennings | |
| 4,485,711 A | 12/1984 | Schnell | |
| 4,603,612 A | 8/1986 | Atkins | |
| 5,018,773 A | 5/1991 | Stavin | |
| 5,341,711 A | 8/1994 | Stay, Jr | |
| 5,634,386 A | 6/1997 | Gasparetto | |
| 5,678,467 A | 10/1997 | Aigner | |
| 5,875,827 A | 3/1999 | Brutscher | |
| 6,135,521 A | 10/2000 | Wirth, Jr. et al. | |
| 6,293,177 B1 | 9/2001 | MacKenzie | |
| 6,732,623 B1 | 5/2004 | Jennings | |
| 7,146,890 B1 | 12/2006 | Rowe | |
| 7,540,224 B2 | 6/2009 | Wang | |
| 7,861,428 B1 | 1/2011 | Clark | |
| 7,886,641 B2 | 2/2011 | Wirth, Jr. et al. | |
| D665,638 S | 8/2012 | Krohmer et al. | |
| 8,826,788 B2 | 9/2014 | Rybka | |
| 9,199,390 B2 | 12/2015 | Wang | |
| 9,707,694 B2 | 7/2017 | Wang | |
| 10,093,737 B2 * | 10/2018 | Zang | C07K 16/2827 |
| 2005/0092152 A1 | 5/2005 | Wirth, Jr. | |
| 2007/0053903 A1 | 3/2007 | Gao et al. | |
| 2008/0248007 A1 | 10/2008 | Chen | |
| 2008/0277024 A1 | 11/2008 | Kozina | |
| 2012/0219559 A1 | 8/2012 | Chen | |
| 2016/0002337 A1 | 1/2016 | Zang | |

FOREIGN PATENT DOCUMENTS

| | | |
|---|---|---|
| WO | 2011020024 A2 | 2/2011 |
| WO | 2014/133728 | 9/2014 |

OTHER PUBLICATIONS

PCT International Search Report and Written Opinion dated Mar. 8, 2007 in connection with PCT International Application No. PCT/US2014/015308, 14 pages.
Krontiris and Capizzi (Internal Medicine, 4th Edition, Editor-in-chief Jay Stein, Elsevier Science, 1994 Chapters 71-72, pp. 699-729).
Carter S. K. et al. (Chemotherapy of Cancer; Second edition; John Wiley & Sons: New York, 1981; appendix C).
Janakiram et al. (Clin Cancer Res, Epub Dec. 30, 2014, 21 (10): 2359-66).
Zhao et al. (PNAS, Jun. 11, 2013, 110 (24): 9879-9884).

\* cited by examiner

*Primary Examiner* — Yan Xiao
(74) *Attorney, Agent, or Firm* — Perkins Coie LLP

(57) ABSTRACT

Provided are methods of treating an autoimmune disease in a subject, or of suppressing transplant rejection in a subject, or of treating a cancer in a subject, as well as compositions therefor.

10 Claims, 7 Drawing Sheets
Specification includes a Sequence Listing.

HHLA2 AS A NOVEL INHIBITOR OF HUMAN IMMUNE SYSTEM AND USES THEREOF

CROSS-REFERENCE TO RELATED APPLICATIONS

This application is a continuation of U.S. patent application Ser. No. 14/770,120, filed Aug. 25, 2015, which is a U.S. National Stage of PCT International Patent Application No. PCT/US2014/015308, filed Feb. 7, 2014, which claims the benefit of U.S. Provisional Patent Application No. 61/771,305, filed Mar. 1, 2013, the contents of each of which are herein incorporated by reference.

STATEMENT OF GOVERNMENT SUPPORT

This invention was made with government support under grant number DK083076 awarded by the National Institutes of Health and grant number W81WH-10-1-0318 awarded by the United States Army Medical Research and Materiel Command. The government has certain rights in the invention.

BACKGROUND OF THE INVENTION

Throughout this application various publications are referred to in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Interactions between members of the B7 ligand and CD28 receptor families generate positive costimulation and negative coinhibition, which are of central importance in regulating T cell responses (1-3). B7-1/B7-2/CD28/CTLA-4 is the most extensively characterized of these pathways. Ligands B7-1 (CD80) and B7-2 (CD86) on antigen-presenting cells (APCs) bind to CD28 on naïve T cells, and provide a major costimulatory signal to activate naïve T cells. After the initial activation, coinhibitory molecule cytotoxic T lymphocyte antigen-4 (CTLA-4, CD152) is induced on T cells and engages the same B7-1 and B7-2 ligands in order to restrain T cell function. In contrast to the costimulatory activity of CD28, the interaction of B7-1 or B7-2 with CTLA-4 is essential for limiting the proliferative response of recently activated T cells to antigen and CD28-mediated costimulation.

During the past decade, several new pathways in the B7 and CD28 families have been identified, including B7h/ICOS, PD-L1/PD-L2/PD-1, B7-H3/receptor and B7x/receptor. B7h (4) (also called ICOS-L, B7RP-1(5), GL50(6), B7H2(7), LCOS(8), and CD275) binds to the inducible costimulator (ICOS, CD278) on activated T cells (9), which induces strong phosphatidylinositol 3-kinase activity (10, 11) and leads to the expression of transcription factors involved in follicular helper CD4 T (Tfh) differentiation (12). Therefore, the B7h/ICOS pathway provides critical T cell help to B cells. Deficiencies in this pathway result in substantially reduced numbers of memory B cells and markedly reduced levels of serum Ig in patients with common variable immunodeficiency (13). In humans, but not in mice, B7h can bind both CD28 and CTLA-4 (14). The B7 family members PD-L1 (15) (also termed B7-H1(16), CD274) and PD-L2 (17) (also called B7-DC(18), CD273) bind to the programmed death 1 receptor (PD-1, CD279), which ultimately decreases induction of cytokines and cell survival proteins in T cells. The PD-L/PD-1 pathway plays an important role in the control of tolerance and autoimmunity (19), and contributes critically to T cell exhaustion and viral persistence during chronic infections (20). In addition, PD-L1 can also bind to B7-1(21).

B7-H3 (22)(CD276) and B7x (23) (also called B7-H4 (24) or B7S1 (25)) are recently discovered members of the B7 family, and their contributions to immune response have not yet been clearly defined. B7-H3 binds activated T cells, but the physiological role of this pathway is unclear, as both costimulatory and coinhibitory effects have been observed (26). B7x binds activated T cells and inhibits T cell functions. In addition, myeloid derived suppressor cells (MDSCs) also express a receptor for B7x (27). Clinical data also support a coinhibitory function for B7x, as aberrant expression of this molecule is observed in many types of human cancers and is often associated with enhanced disease progression and poor clinical outcome (28). It appears that the B7x pathway is exploited as part of the immune evasion mechanisms used by many human cancers. Collectively, the regulated spatial and temporal expression of costimulatory and coinhibitory B7 molecules provides the controls that underlie T cell-mediated immune responses.

Due to their fundamental biological importance and therapeutic potential, there has been considerable interest in the identification of additional molecules with costimulatory or coinhibitory function.

The present invention addresses the need for improved therapies and therapeutics based on a novel B7/CD28 family pathway, namely, a HERV-H LTR Associating Protein 2 (HHLA2) pathway.

SUMMARY OF THE INVENTION

A method is provided of treating an autoimmune disease in a subject, or of suppressing transplant rejection in a subject, comprising administering to the subject an amount of an HHLA2-immunoglobulin-fusion protein effective to treat an autoimmune disease, or suppress transplant rejection, respectively.

Also provided is a method of treating a cancer in a subject, comprising administering to the subject an amount of an anti-HHLA2 antibody, or an HHLA2-binding fragment of an anti-HHLA2 antibody, effective to treat a cancer.

Also provided is a method of treating an infectious disease a subject, comprising administering to the subject an amount of an anti-HHLA2 antibody, or an HHLA2-binding fragment of an anti-HHLA2 antibody, effective to an infectious disease.

Also provided is a composition comprising an HHLA2-immunoglobulin-fusion protein and a pharmaceutically acceptable carrier.

Also provided is a composition comprising an anti-HHLA2 antibody, or an HHLA2-binding fragment of such an antibody, and a pharmaceutically acceptable carrier.

Also provided is an HHLA2-immunoglobulin-fusion protein for treating an autoimmune disease in a subject, or for suppressing transplant rejection in a subject.

Also provided is an anti-HHLA2 antibody, or an HHLA2-binding fragment of such an antibody, for treating a cancer in a subject.

Also provided is a screening method for identifying an agent as a treatment for an autoimmune disease in a subject, or as a treatment for suppressing transplant rejection in a subject, comprising contacting an immune system cell expressing an HHLA2 receptor with the agent and quantifying activity of the cell in the presence and the absence of the agent, and identifying the agent as a treatment for an autoimmune disease in a subject, or as a treatment for suppressing transplant rejection in a subject, wherein an agent that inhibits the activity of the cell in its presence as compared to in its absence is indicated to be a treatment for an autoimmune disease in a subject or a treatment for suppressing transplant rejection in a subject, and an agent that does not affect activity of, or stimulates activity of, the cell its presence as compared to in its absence is not indicated to be a treatment for an autoimmune disease in a subject or a treatment for suppressing transplant rejection in a subject.

Also provided is a screening method for identifying an agent as a treatment for a cancer or for an infectious disease, comprising contacting an HHLA2 receptor with the agent and an amount of HHLA2 and quantifying the antagonism of the agent on HHLA2 binding to the HHLA2 receptor, and identifying the agent as a treatment for a cancer or for an infectious disease, wherein an agent that competes with, and/or reduces, HHLA2 binding to the HHLA2 receptor in its presence as compared to in its absence is indicated to be a treatment for a cancer or an infectious disease, and an agent that does not affect HHLA2 binding in its presence as compared to in its absence is not indicated to be a treatment for a cancer or for an infectious disease. In an embodiment, the HHLA2 receptor is expressed on a cell. In an embodiment, the cell is an immune system cell. In an embodiment, the cell is CD4 T cell, a CD9 T cell or an antigen-presenting cell.

DETAILED DESCRIPTION OF THE INVENTION

Figures 1A, 1B, 1C:
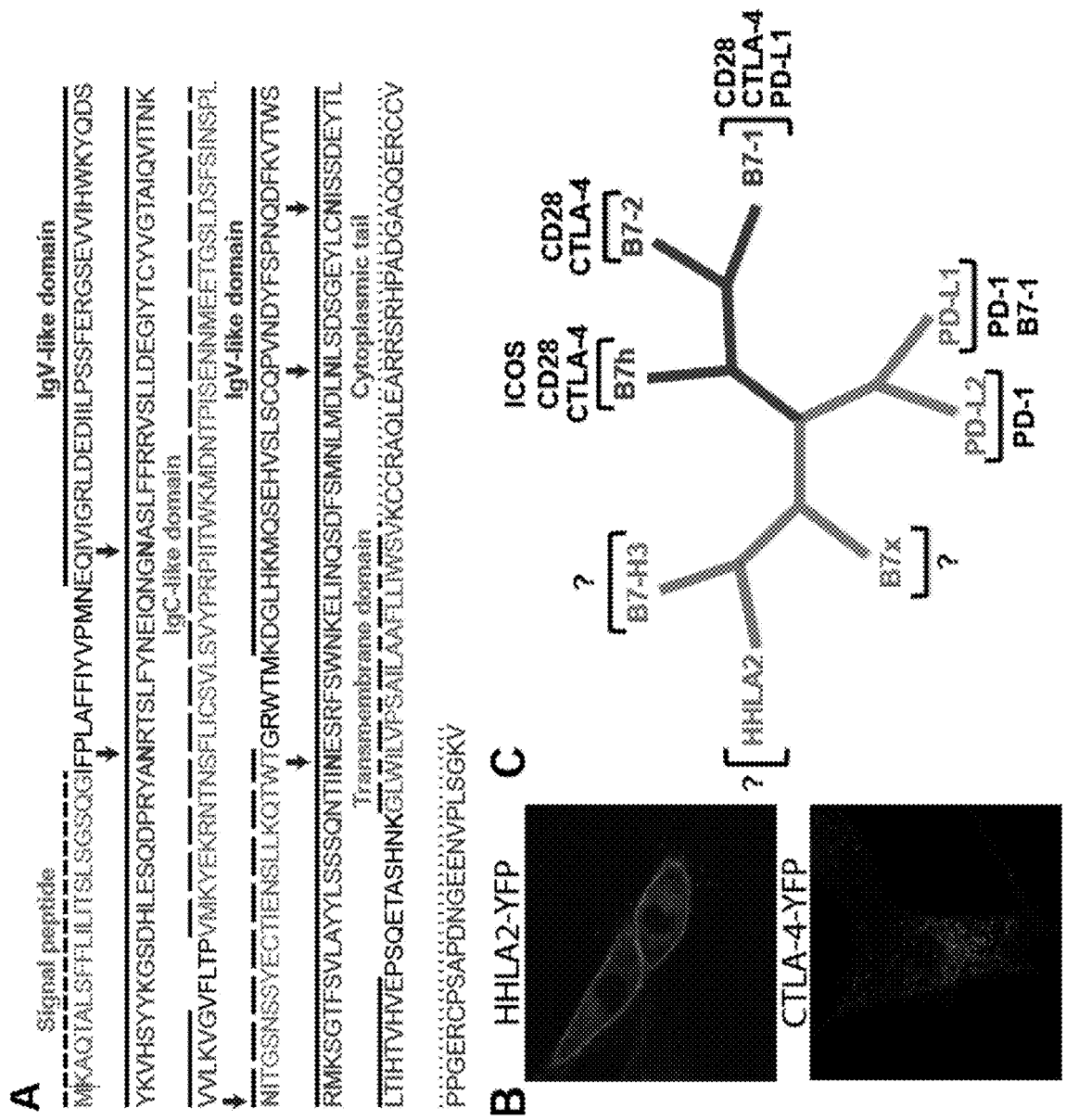
FIG. 1A-1C. HHLA2 is a member of the B7 family and forms a group with B7x and B7-H3. (A) Predicted signal peptide, IgV-like and IgC-like domains, transmembrane region, and cytoplasmic tail of human HHLA2 protein (SEQ ID NO: 1) were indicated. The potential N-glycosylation sites were arrowed. (B) Confocal microscopy showed that human HHLA2-YFP protein (YFP=Yellow Fluorescent protein) was predominantly expressed on cell membranes of the 3T3 cells, whereas human CTLA-4-YFP fusion protein was mainly localized intracellularly in the 3T3 cells. (C) Phylogenetic tree of the human B7 family. The phylogenetic comparison of human B7 molecules was generated by PAUP version 4.0b10. The family was divided into three groups: HHLA2, B7x, and B7-H3 for group III; PD-L1 and PD-L2 for group II; B7-1, B7-2, and B7h for group I. Receptors for human B7 molecules are also indicated.

A method is provided of treating an autoimmune disease in a subject, or of suppressing transplant rejection in a subject, comprising administering to the subject an amount of an HHLA2-immunoglobulin-fusion protein effective to treat an autoimmune disease, or suppress transplant rejection, respectively.

In an embodiment, the method is of treating an autoimmune disease.

As used herein, autoimmune diseases treatable by the method include acute disseminated encephalomyelitis (ADEM), alopecia areata, antiphospholipid syndrome, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Behcet's disease, celiac disease, Chagas disease, cold agglutinin disease, Crohn's disease, dermatomyositis, diabetes mellitus type 1, eosinophilic fasciitis, gastrointestinal pemphigoid, Goodpasture's syndrome, Grave's syndrome, Guillain-Barré syndrome, Hashimoto's encephalopathy, Hashimoto's thyroiditis, lupus erythematosus, Miller-Fisher syndrome, mixed connective tissue disease, myasthenia gravis, pemphigus vulgaris, pernicious anaemia, polymyositis, psoriasis, psoriatic arthritis, relapsing polychondritis, rheumatoid arthritis, rheumatic fever, Sjögren's syndrome, temporal arteritis, transverse myelitis, ulcerative colitis, undifferentiated connective tissue disease, vasculitis, and Wegener's granulomatosis.

In an embodiment, the autoimmune disease treated is adult rheumatoid arthritis.

In an embodiment, the method is of suppressing transplant rejection. The method treats graft versus host disease, for example where stem cells or bone marrow is transplanted. In an embodiment, the transplant rejection suppressed is a kidney transplant rejection. In an embodiment, the transplant rejection suppressed is a lung, heart, pancreas, cornea, or liver transplant rejection.

In an embodiment, the HHLA2-immunoglobulin-fusion protein comprises an extracellular domain of human HHLA2. In an embodiment, the extracellular domain comprises the sequence set forth in SEQ ID NO:1 but excluding the signal peptide, transmembrane domain and cytoplasmic tail. In an embodiment, the HHLA2-immunoglobulin-fusion protein comprises a human IgG Fc region. In an embodiment, the HHLA2-immunoglobulin-fusion protein comprises a human IgM Fc region. In an embodiment, the IgG is an IgG1. In an embodiment, the HHLA2-immunoglobulin-fusion protein comprises the consecutive amino acid residues set forth in SEQ ID NO:2.

In an embodiment, the methods can be performed, mutatis mutandis, wherein a nucleic acid encoding an HHLA2-Ig is administered in a fashion such that it can express inside the subject, in place of the HHLA2-Ig fusion protein. In an embodiment of this method, the nucleic acid sequence comprises the following (SEQ ID NO:3):

atgaagttatgcatattactggccgtcgtggcctttgttggcctctcgc tcgggagatctttggctttcttcatttatgttcctatgaatgaacaaat cgtcattggaagacttgatgaagatataattctcccttcttcatttgag aggggatccgaagtcgtaatacactggaagtatcaagatagctataagg ttcatagttactacaaaggcagtgaccatttggaaagccaagatcccag atatgcaaacaggacatccctttctataatgagattcaaaatgggaat gcgtcactattttcagaagagtaagccttctggacgaaggaatttaca cctgctatgtaggaacagcaattcaagtgattacaaacaaagtggtgct aaaggtgggagttttctcacacccgtgatgaagtatgaaaagaggaac acaaacagcttcttaatatgcagcgtgttaagtgtttatcctcgtccaa ttatcacgtggaaaatggacaacacacctatctctgaaaacaacatgga agaaacagggtctttggattcttttctattaacagcccactgaatatt acaggatcaaattcatcttatgaatgtacaattgaaaattcactgctga agcaaacatggacagggcgctggacgatgaaagatggccttcataaaat gcaaagtgaacacgtttcactctcatgtcaacctgtaaatgattatttt tcaccaaaccaagacttcaaagttacttggtccagaatgaaaagtggga ctttctctgtcctggcttactatctgagctcctcacaaaatacaattat caatgaatcccgattctcatggaacaaagagctgataaaccagagtgac ttctctatgaatttgatggatcttaatctttcagacagtggggaatatt tatgcaatatttcttcggatgaatatactttacttaccatccacacagt gcatgtagaaccgagccaagaaacagcttccggcggccgctctaaaact agtggatccgagcccaaatcttgtgacaaaactcacacatgcccaccgt gcccagcacctgaactcctgggggaccgtcagtcttcctcttcccccc aaacccaaggacacccctcatgatctcccggacccctgaggtcacatgc gtggtggtggacgtgagccacgaagaccctgaggtcaagttcaactggt acgtggacggcgtggaggtgcataatgccaagacaaagccgcgggagga gcagtacaacagcacgtaccgtgtggtcagcgtcctcaccgtcctgcac caggactggctgaatggcaaggagtacaagtgcaaggtctccaacaaag ccctcccagccccatcgagaaaaccatctccaaagccaaagggcagcc ccgagaaccacaggtgtacaccctgcccccatcccgggaggagatgacc aagaaccaggtcagcctgacctgcctggtcaaaggcttctatcccagcg acatcgccgtggagtgggagagcaatgggcagccggagaacaactacaa gaccacgcctcccgtgctggactccgacggctccttcttcctctatagc aagctcaccgtggacaagagcaggtggcagcaggggaacgtcttctcat gctccgtgatgcatgaggctctgcacaaccactacacgcagaagagcct ctccctgtctccgggtaaa.

In an embodiment, of all aspects of the invention described herein reciting a subject, the subject is a human. In an embodiment, of all aspects of the invention described herein reciting HHLA2, the HHLA2 is a human HHLA2. In an embodiment, of all aspects of the invention described herein reciting an anti-HHLA2 antibody (or fragment thereof), the HHLA2 to which the antibody is directed (targeted) is a human HHLA2.

In an embodiment, the HHLA2 is a human HHLA2 comprising the following sequence (SEQ ID NO:1)

MKAQTALSFFLILITSLSGSQGIFPLAFFIYVPMNEQIVIGRLDEDIIL

PSSFERGSEVVIHWKYQDSYKVHSYYKGSDHLESQDPRYANRTSLFYNE

```
IQNGNASLFFRRVSLLDEGIYTCYVGTAIQVITNKVVLKVGVFLTPVMK

YEKRNTNSFLICSVLSVYPRPIITWKMDNTPISENNMEETGSLDSFSIN

SPLNITGSNSSYECTIENSLLKQTWTGRWTMKDGLHKMQSEHVSLSCQP

VNDYFSPNQDFKVTWSRMKSGTFSVLAYYLSSSQNTTINESRFSWNKEL

INQSDFSMNLMDLNLSDSGEYLCNISSDEYTLLTIHTVHVEPSQETASH

NKGLWILVPSAILAAFLLIWSVKCCRAQLEARRSRHPADGAQQERCCVP

PGERCPSAPDNGEENVPLSGKV
```

In an embodiment, the HHLA2-immunoglobulin-fusion protein is an HHLA2-IgG comprising the following sequence (SEQ ID NO:2)

```
RSLAFFIYVPMNEQIVIGRLDEDIILPSSFERGSEVVIHWKYQDSYKVH

SYYKGSDHLESQDPRYANRTSLEYNEIQNGNASLFERRVSLLDEGIYTC

YVGTAIQVITNKVVLKVGVFLTPVMKYEKRNTNSFLICSVLSVYPRPII

TWKMDNTPISENNMEETGSLDSFSINSPLNITGSNSSYECTIENSLLKQ

TWTGRWTMKDGLHKMQSEHVSLSCQPVNDYFSPNQDFKVTWSRMKSGTF

SVLAYYLSSSQNTTINESRFSWNKELINQSDFSMNLMDLNLSDSGEYLC

NISSDEYTLLTIHTVHVEPSQETASGGRSKTSGSEPKSCDKTHTCPPCP

APELLGGPSVFLEPPKPKDTLMISRTPEVTCVVVDVSHEDPEVKFNWYV

DGVEVHNAKTKPREEQYNSTYRVVSVLTVLHQDWLNGKEYKCKVSNKAL

PAPIEKTISKAKGQPREPQVYTLPPSREEMTKNQVSLTCLVKGEYPSDI

AVEWESNGQPENNYKTTPPVLDSDGSFFLYSKLTVDKSRWQQGNVFSCS

VMHEALHNHYTQKSLSLSPGK.
```

In an embodiment, an HHLA2 receptor as described herein has the same, or has 99% or more sequence identity to, an HHLA2 receptor on a human T cell or a human antigen presenting cell.

Also provided is a method of treating a cancer in a subject, comprising administering to the subject an amount of an anti-HHLA2 antibody, or an HHLA2-binding fragment of an anti-HHLA2 antibody, effective to treat a cancer.

There are at least two mechanisms by which an anti-HHLA2 antibody, or HHLA2-binding fragment thereof, and compositions comprising such, can treat a cancer: 1) the antibody or fragment can block the inhibition of HHLA2 expressed on immune cells; and 2) the antibody or fragment can block the inhibition of HHLA2 expressed on cancer cells. These two mechanisms can exist at the same time. Moreover, the cancer cells, such as tumor cells, do not need to be HHLA2 positive.

Cancers, including tumors, treatable by the invention include of the nasopharynx, pharynx, lung, bone, brain, sialaden, stomach, esophagus, testes, ovary, uterus, endometrium, liver, small intestine, appendix, colon, rectum, gall bladder, pancreas, kidney, urinary bladder, breast, cervix, vagina, vulva, prostate, thyroid, skin, or is a glioma. In an embodiment, the cancer treated is a metastatic melanoma. In an embodiment, the cancer treated comprises a tumor. In an embodiment, the cancer treated comprises a HHLA2-bearing tumor.

A method is provided for treating a cancer in a subject comprising administering to the subject an anti-HHLA2 antibody, or antigen-binding fragment thereof, or HHLA2-binding aptamer, or isolated HHLA2 receptor protein, in an amount effective to treat a cancer in a subject. In an embodiment, the subject is a human subject. In an embodiment, the anti-HHLA2 antibody, or antigen-binding fragment thereof, or HHLA2-binding aptamer, or isolated HHLA2 receptor protein, has a cytotoxic agent attached thereto. In an embodiment, the anti-HHLA2 antibody, or antigen-binding fragment thereof, or HHLA2-binding aptamer, has an anti-cancer drug conjugated thereto. In an embodiment, the anti-HHLA2 antibody, or antigen-binding fragment thereof, or HHLA2-binding aptamer, or isolated HHLA2 receptor protein, has a chemotherapeutic agent attached thereto. In an embodiment, the antigen-binding fragment of an anti-HHLA2 antibody is administered. In an embodiment, the antigen-binding fragment of an anti-HHLA2 antibody is administered as a fusion protein. In an embodiment, the isolated HHLA2 receptor protein is administered. In an embodiment, the isolated HHLA2 receptor protein is administered as a fusion protein. In an embodiment, the fusion protein comprises the antigen-binding fragment of an anti-HHLA2 antibody bound via a peptide bond to an immunoglobulin Fc region. In an embodiment, the immunoglobulin Fc region is an immunoglobulin G Fc region or an immunoglobulin M Fc region. In an embodiment, the fusion protein comprises the isolated HHLA2 receptor protein bound via a peptide bond to an immunoglobulin Fc region. In an embodiment, the immunoglobulin Fc region is an immunoglobulin G Fc region or an immunoglobulin M Fc region. In an embodiment, the anti-HHLA2 antibody, or antigen-binding fragment thereof, is administered as a mammalian dendritic cell loaded with the anti-HHLA2 antibody, or antigen-binding fragment thereof. In an embodiment, the cancer is a cancer of the lung, thyroid, breast, ovary, pancreas, esophagus, kidney, liver, bladder, prostate, a melanoma, or a hematological malignancy. In an embodiment, the cancer is a hematological malignancy which is a lymphoma or a leukemia.

In an embodiment of the methods, the HHLA2 is a human HHLA2 protein. In an embodiment of the methods, the HHLA2 protein comprises consecutive amino acid residues having the sequence set forth in SEQ ID NO:1. In an embodiment of the methods, the antibody is a humanized antibody, a chimeric antibody or an isolated human antibody. In an embodiment of the methods, the antibody is a monoclonal antibody.

Also provided is a method of treating an infectious disease a subject, comprising administering to the subject an amount of an anti-HHLA2 antibody, or an HHLA2-binding fragment of an anti-HHLA2 antibody, effective to an infectious disease. In an embodiment of the methods, the HHLA2 is a human HHLA2 protein. In an embodiment of the methods, the HHLA2 protein comprises consecutive amino acid residues having the sequence set forth in SEQ ID NO:1. In an embodiment of the methods, the antibody is a humanized antibody, a chimeric antibody or an isolated human antibody. In an embodiment of the methods, the antibody is a monoclonal antibody.

A method for identifying a biological sample as cancerous comprising contacting the sample with an anti-HHLA2 antibody, or antigen-binding fragment thereof, having a detectable probe molecule attached thereto and determining if the anti-HHLA2 antibody, or antigen-binding fragment thereof, having a detectable probe localizes to the sample by detecting the probe.

In an embodiment, the probe is a fluorophore, a non-fluorescent dye, a radioactive isotope, a fluorescent protein, an enzyme, or a magnetic or paramagnetic entity. In an embodiment, the biological sample comprises a tissue. In an embodiment, the biological sample comprises a cell.

In an embodiment, the biological sample is within a subject and the anti-HHLA2 antibody, or antigen-binding fragment thereof, having a detectable probe attached thereto is administered to the subject. In an embodiment, the biological sample has been obtained from a subject and the sample is directly contacted with the anti-HHLA2 antibody, or antigen-binding fragment thereof, having a detectable probe attached thereto. In an embodiment, the biological sample is a lung, thyroid, breast, ovary, pancreas, melanoma, esophagus, kidney, liver, bladder, or prostate sample. In an embodiment, the biological sample is determined as cancerous if the HHLA2 antibody, or antigen-binding fragment thereof, having a detectable probe localizes to the sample.

In an embodiment, the biological sample is determined as cancerous if the amount of HHLA2 antibody, or antigen-binding fragment thereof, having a detectable probe localizing to the sample is greater than a predetermined control amount. The concept of a control, for example corresponding to an equivalent non-cancerous sample, is well-established in the art. In an embodiment, the biological sample is determined as cancerous if the sample mark's positive for HHLA2. In an embodiment, the sample is a sample taken from a tissue listed as positive for HHLA2 expression in Table 3. In an embodiment, samples taken from a tissue listed as negative for HHLA2 expression in Table 3 are excluded.

As used in the methods herein, the term "antibody" refers to an intact antibody, i.e. with complete Fc and Fv regions. "Fragment" refers to any portion of an antibody, or portions of an antibody linked together, such as, in non-limiting examples, a Fab, F(ab)$_2$, a single-chain Fv (scFv), which is less than the whole antibody but which is an antigen-binding portion and which competes with the intact antibody of which it is a fragment for specific binding. As such a fragment can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')$_2$, F$_d$, F$_v$, complementarity determining region (CDR) fragment, single-chain antibody (scFv), (a variable domain light chain (V$_L$) and a variable domain heavy chain (V$_H$) linked via a peptide linker. In an embodiment the linker of the scFv is 10-25 amino acids in length. In an embodiment the peptide linker comprises glycine, serine and/or threonine residues. For example, see Bird et al., Science, 242: 423-426 (1988) and Huston et al., Proc. Natl. Acad. Sci. USA, 85:5879-5883 (1988) each of which are hereby incorporated by reference in their entirety), or a polypeptide that contains at least a portion of an antibody that is sufficient to confer HHLA2-specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342: 878-883 (1989), each of which are hereby incorporated by reference in their entirety). As used herein, the term "polypeptide" encompasses native or artificial proteins, protein fragments and polypeptide analogs of a protein sequence. A polypeptide may be monomeric or polymeric. As used herein, an F$_d$ fragment means an antibody fragment that consists of the V$_H$ and CH1 domains; an F$_v$ fragment consists of the V$_1$ and V$_H$ domains of a single arm of an antibody; and a dAb fragment (Ward et al., Nature 341:544-546 (1989) hereby incorporated by reference in its entirety) consists of a V$_H$ domain. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target HHLA2 (or an HHLA2 receptor, as applicable), wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus an identified monoclonal antibody can be produced by non-hybridoma techniques, e.g. by appropriate recombinant means once the sequence thereof is identified.

In an embodiment of the inventions described herein, the antibody is isolated. As used herein, the term "isolated antibody" refers to an antibody that by virtue of its origin or source of derivation has one, two, three or four of the following: (1) is not associated with naturally associated components that accompany it in its native state, (2) is free of other proteins from the same species, (3) is expressed by a cell from a different species, and (4) does not otherwise occur in nature without the hand of man.

In an embodiment the composition or pharmaceutical composition comprising one or more of the antibodies or fragments described herein is substantially pure with regard to the antibody or fragment. A composition or pharmaceutical composition comprising one or more of the antibodies or fragments described herein is "substantially pure" with regard to the antibody or fragment when at least about 60 to 75% of a sample of the composition or pharmaceutical composition exhibits a single species of the antibody or fragment. A substantially pure composition or pharmaceutical composition comprising one or more of the antibodies or fragments described herein can comprise, in the portion thereof which is the antibody or fragment, 60%, 70%, 80% or 90% of the antibody or fragment of the single species, more usually about 95%, and preferably over 99%. Antibody purity or homogeneity may tested by a number of means well known in the art, such as polyacrylamide gel electrophoresis or HPLC.

As used herein, a "human antibody" unless otherwise indicated is one whose sequences correspond to (i.e. are identical in sequence to) an antibody that could be produced by a human and/or has been made using any of the techniques for making human antibodies as disclosed herein, but not one which has been made in a human. This definition of a human antibody specifically excludes a humanized antibody. A "human antibody" as used herein can be produced using various techniques known in the art, including phage-display libraries (e.g. Hoogenboom and Winter, J. Mol. Biol., 227:381 (1991); Marks et al., J. Mol. Biol., 222:581 (1991), hereby incorporated by reference in its entirety), by methods described in Cole et al., Monoclonal Antibodies and Cancer Therapy, Alan R. Liss, p. 77 (1985) (hereby incorporated by reference in its entirety); Boerner et al., J. Immunol., 147(1):86-95 (1991) (hereby incorporated by reference in its entirety), van Dijk and van de Winkel, Curr. Opin. Pharmacol., 5: 368-74 (2001) (hereby incorporated by reference in its entirety), and by administering the antigen (e.g. HHLA2) to a transgenic animal that has been modified to produce such antibodies in response to antigenic challenge, but whose endogenous loci have been disabled, e.g., immunized xenomice (see, e.g., U.S. Pat. Nos. 5,939,598; 6,075,181; 6,114,598; 6,150,584 and 6,162,963 to Kucherlapati et al. regarding XENOMOUSE™ technology, each of which patents are hereby incorporated by reference in their entirety), e.g. VelocImmune® (Regeneron, Tarrytown, N.Y.), e.g. UltiMab® platform (Medarex, now Bristol Myers Squibb, Princeton, N.J.). See also, for example, Li et al., Proc. Natl. Acad. Sci. USA, 103:3557-3562 (2006) regarding human antibodies generated via a human B-cell hybridoma technology. See also KM Mouse® system, described in PCT Publication WO 02/43478 by Ishida et al., in which the mouse carries a human heavy chain transchromosome and a human light chain transgene, and the TC mouse system, described in Tomizuka et al. (2000) Proc. Natl. Acad. Sci. USA 97:722-727, in which the mouse carries both a human heavy chain transchromosome and a human light chain transchromosome, both of which are hereby incorporated by reference in their entirety. In each of these systems, the transgenes and/or transchromosomes carried by the mice comprise human immunoglobulin variable and constant region sequences.

The term "human antibody", as used herein, is intended to include antibodies having variable regions in which both the framework and CDR regions are sequences of human origin or identical thereto other than antibodies naturally occurring in a human or made in a human. Furthermore, if the antibody (e.g. an intact antibody rather than, for example, an Fab fragment) contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. In one non-limiting embodiment, where the human antibodies are human monoclonal antibodies, such antibodies can be produced by a hybridoma which includes a B cell obtained from a transgenic nonhuman animal, e.g., a transgenic mouse, having a genome comprising a human heavy chain transgene and a light chain transgene fused to an immortalized cell.

In an embodiment, the anti-HHLA2 antibody described herein is a recombinant human antibody. The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin variable domain are replaced by corresponding non-human residues. These modifications may be made to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are described in U.S. Pat. Nos. 4,816,567; 5,807,715; 5,866,692; 6,331,415; 5,530,101; 5,693,761; 5,693,762; 5,585, 089; and 6,180,370, the content of each of which is hereby incorporated by reference in its entirety.

A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in their entirety).

Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

In an embodiment, the anti-HHLA2 antibody described herein (or fragment thereof) is capable of specifically binding HHLA2 or specifically binds an HHLA2. IN an embodiment, the HHLA2 is human a HHLA 2. As used herein, the terms "is capable of specifically binding" or "specifically binds" refers to the property of an antibody or fragment of binding to the (specified) antigen with a dissociation constant that is <1 µM, preferably <1 nM and most preferably <10 pM. In an embodiment, the Kd of the antibody (or fragment) for HHLA2 is 250-500 pM. An epitope that "specifically binds" to an antibody or a polypeptide is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a HHLA2 conformational epitope is an antibody that binds this epitope with greater affinity, avidity, more readily, and/or with greater duration than it binds to other HHLA2 epitopes or non-HHLA2 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding.

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG2a, human IgG2b, human IgG3 or human IgG4. A combination of any of these antibodies subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the $V_H$ (H1, H2, H3) and three in the $V_L$ (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal cysteine.

Compositions or pharmaceutical compositions comprising the antibodies, ScFvs or fragments of antibodies disclosed herein are preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for parenteral administration, including intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the can comprise one or more of dibasic sodium phosphate, potassium chloride, monobasic potassium phosphate, polysorbate 80 (e.g. 2-[2-[3,5-bis(2-hydroxyethoxy) oxolan-2-yl]-2-(2-hydroxyethoxy)ethoxy]ethyl (E)-octadec-9-enoate), disodium edetate dehydrate, sucrose, monobasic sodium phosphate monohydrate, and dibasic sodium phosphate dihydrate.

The antibodies, or fragments of antibodies, or compositions, or pharmaceutical compositions described herein can also be lyophilized or provided in any suitable forms including, but not limited to, injectable solutions or inhalable solutions, gel forms and tablet forms.

The term "Kd", as used herein, is intended to refer to the dissociation constant of an antibody-antigen interaction.

One way of determining the Kd or binding affinity of antibodies to HHLA2 is by measuring binding affinity of monofunctional Fab fragments of the antibody. (The affinity constant is the inverted dissociation constant). To obtain monofunctional Fab fragments, an antibody (for example, IgG) can be cleaved with papain or expressed recombinantly. The affinity of an anti-HHLA2 Fab fragment of an antibody can be determined by surface plasmon resonance (BIAcore3000™ surface plasmon resonance (SPR) system, BIAcore Inc., Piscataway N.J.). CM5 chips can be activated with N-ethyl-N'-(3-dimethylaminopropyl)-carbodiinide hydrochloride (EDC) and N-hydroxysuccinimide (NHS) according to the supplier's instructions. HHLA2 can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10x estimated Kd) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant (Kd) values are calculated as $k_{off}/k_{on}$. This protocol is suitable for use in determining binding affinity of an antibody or fragment to any HHLA2. Other protocols known in the art may also be used. For example, ELISA of HHLA2 with mAb can be used to determine the kD values. The Kd values reported herein used this ELISA-based protocol.

Also provided is a composition comprising an HHLA2-immunoglobulin-fusion protein bound to an HHLA2 receptor on an immune system cell. In an embodiment, the HHLA2-immunoglobulin-fusion protein comprises the extracellular domain of human HHLA2. In an embodiment, the HHLA2-immunoglobulin-fusion protein comprises a human IgG Fc region. In an embodiment, the IgG is an IgG1. In an embodiment, the immune system cell is a CD4 T cell, an CD8 T cell, or an antigen-presenting cell. In an embodiment, the immune system cell is human.

Also provided is a composition comprising an HHLA2-immunoglobulin-fusion protein and a pharmaceutically acceptable carrier. In an embodiment, HHLA2-immunoglobulin-fusion protein comprises an extracellular domain of human HHLA2. In an embodiment, HHLA2-immunoglobulin-fusion protein comprises a human IgG Fc region. In an embodiment, the IgG is an IgG1. In an embodiment, the HHLA2-immunoglobulin-fusion protein comprises the consecutive amino acid residues set forth in SEQ ID NO:2. In an embodiment, the composition is a pharmaceutical composition.

Also provided is a composition comprising an anti-HHLA2 antibody, or an HHLA2-binding fragment of such an antibody, and a pharmaceutically acceptable carrier. In an embodiment, the HHLA2 is a human HHLA2 protein. In an embodiment, the HHLA2 protein comprises consecutive amino acid residues having the sequence set forth in SEQ ID NO:1. In an embodiment, the antibody is a humanized antibody, a chimeric antibody or an isolated human antibody. In an embodiment, the antibody is a monoclonal antibody. In an embodiment, the composition is a pharmaceutical composition.

Also provided is an HHLA2-immunoglobulin-fusion protein for treating an autoimmune disease in a subject, or for suppressing transplant rejection in a subject.

Also provided is an anti-HHLA2 antibody, or an HHLA2-binding fragment of such an antibody, for treating a cancer in a subject.

Also provided is a screening method for identifying an agent as a treatment for an autoimmune disease in a subject, or as a treatment for suppressing transplant rejection in a subject, comprising contacting an immune system cell expressing an HHLA2 receptor with the agent and quantifying activity of the cell in the presence and the absence of the agent, and identifying the agent as a treatment for an autoimmune disease in a subject, or as a treatment for suppressing transplant rejection in a subject,
wherein an agent that inhibits the activity of the cell in its presence as compared to in its absence is indicated to be a treatment for an autoimmune disease in a subject or a treatment for suppressing transplant rejection in a subject, and an agent that does not affect activity of, or stimulates activity of, the cell its presence as compared to in its absence is not indicated to be a treatment for an autoimmune disease in a subject or a treatment for suppressing transplant rejection in a subject.

Also provided is a screening method for identifying an agent as a treatment for a cancer or for an infectious disease, comprising contacting an HHLA2 receptor with the agent and an amount of HHLA2 and quantifying the antagonism of the agent on HHLA2 binding to the HHLA2 receptor, and identifying the agent as a treatment for a cancer or for an infectious disease,
wherein an agent that competes with, and/or reduces, HHLA2 binding to the HHLA2 receptor in its presence as compared to in its absence is indicated to be a treatment for a cancer or an infectious disease, and an agent that does not affect HHLA2 binding in its presence as compared to in its absence is not indicated to be a treatment for a cancer or for an infectious disease. In an embodiment, the HHLA2 receptor is expressed on a cell. In an embodiment, the cell is an immune system cell. In an embodiment, the cell is CD4 T cell, a CD9 T cell or an antigen-presenting cell.

In an embodiment of the screening methods, the agent is an organic molecule of 2000 daltons or less, an antibody, an antigen-binding fragment of an antibody, and siRNA nucleic acid, a polypeptide of less than 200 residues or an aptamer.

In an embodiment, "determining" as used herein means experimentally determining.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Here the HERV-HLTR-associating 2 (HHLA2) (29) is described as a member of the B7 family with coinhibitory function for both human CD4 and CD8 T cells, which is comparable to other important family members. A putative receptor for HHLA2 is expressed widely on T cells and APCs.

Results

Characterization of HHLA2 as a B7 family member: In a homology search of various databases using amino acid sequences of human B7x and B7-H3, HHLA2 was identified which was shown previously to share significant homology with the B7 family (29, 30) and was also called B7H7(30). The human HHLA2 gene is located in the q13.13 region of the chromosome 3 and is near the B7-1 and B7-2 genes (q13.3-q21). The open reading frame was sequenced and the deduced protein sequence of HHLA2 was found to contain 414 amino acids (FIG. 1A), longer than most B7 members, but shorter than human B7-H3. HHLA2 shares varying levels of amino acid identity and similarity with human B7-1 (10% and 23%), B7-2 (13% and 29%), B7h (15% and 30%), PD-L1 (12% and 26%), PD-L2 (14% and 27%), B7-H3 long form (15% and 31%) and short form (16% and 33%), and B7x (18% and 30%), which are comparable to the homologies exhibited by other members of the family; for example, B7-1, the founding member of the B7 family, shares 13-21% of amino acid identity and 22-37% of similarity with other human B7 molecules.

The putative HHLA2 protein has an N-terminal signal peptide, an ectodomain composed of tandem IgV-IgC-IgV domains, six potential sites for N-linked glycosylation, a transmembrane region, and a 49-aa cytoplasmic tail (FIG. 1A). The predicted HHLA2 protein is a type I transmembrane molecule. To test this prediction, the HHLA2 protein localization was examined by expressing HHLA2-YFP fusion protein in the 3T3 cell line which did not express endogenous HHLA2. Confocal microscopy analysis revealed that HHLA2 protein was predominantly found on cell membranes with some in the cytoplasm (FIG. 1B). In contrast, human CTLA-4-YFP fusion protein was mainly localized intracellularly in the 3T3 cell (FIG. 1B).

Evolution of HHLA2: In a previous study the B7 family of proteins was divided into three groups by phylogenetic analysis (23). With HHLA2 added into this family, PAUP 4.0b10 (31) was used to reevaluate the relationship among human B7 proteins. As shown in FIG. 1C, a phylogenetic comparison of the family divided the human B7 molecules into three groups: group I includes B7-1, B7-2, and B7h; group II consists of PD-L1 and PD-L2; and group III contains B7x, HHLA2 and B7-H3. For group I, CD28 and CTLA-4 are receptors for all three B7 molecules and the closely related ICOS is a receptor for B7h, whereas PD-L1 can bind B7-1. For group II, PD-1 is the receptor for both PD-L1 and PD-L2. For group III, receptors have not been identified yet. The phylogenetic comparison suggests that receptors for group III would not be real homologues of receptors for group I and II.

Based on sequence analyses, putative HHLA2 orthologs appear to be present in wide range of species, including fish (GeneBank accession number ACH85300), frog (NP_001122116), Heterocephalus glaber (EHB18400), giant panda (EFB27984), and monkey (EHH16036 and EHH51009), suggesting evolutionarily conserved function. However, in contrast to other B7 family members, laboratory mouse and rat strains do not express HHLA2, which makes it the first B7 family member expressed in human but not in mouse.

Figures 2A, 2B:
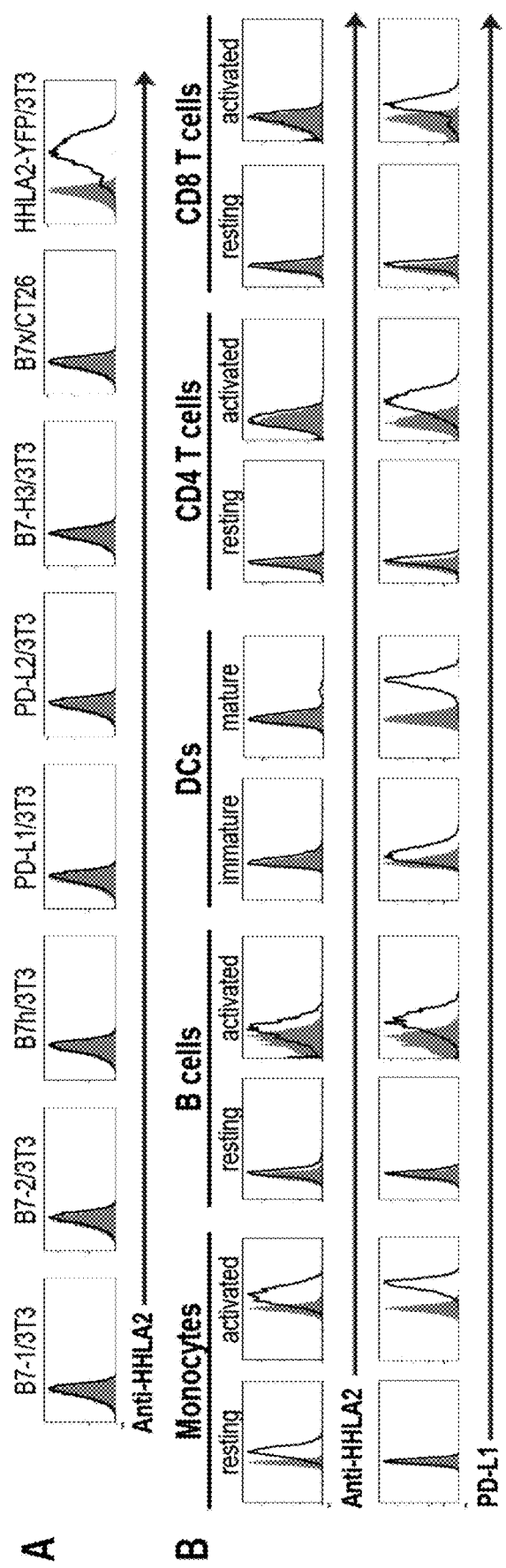
FIG. 2A-2B. Analysis of endogenous HHLA2 protein expression by flow cytometry with specific mAb. (A) 3T3 or CT26 cells were transfected with MSCV vectors to stably express cell surface human B7-1, B7-2, B7h, PD-L1, PD-L2, B7-H3, B7x, and HHLA2-YFP. Transfectants were stained with an anti-HHLA2 mAb clone 566.1 (open histograms) or isotype control (shaded histograms) for FACS. (B) Human peripheral blood mononuclear cells (PBMCs) were stained with biotin-anti-HHLA2 mAb/APC-streptavidin, and PE-, FITC-, or Percp-Cy5.5-conjugated anti-CD14 (monocytes), anti-CD19 (B cells), anti-CD4, anti-CD8, and anti-PD-L1. Monocytes and B cells were activated with LPS/IFN-γ for three days, whereas T cells were activated with anti-CD3 for three days. Immature dendritic cells (DCs) were generated from blood monocytes incubated with GM-CSF/IL-4 and were induced with LPS/IFN-γ to become mature DCs. Endogenous HHLA2 protein was highly detected on monocytes and induced on B cells, whereas PD-L1 was induced only on activated immune cells. Anti-HHLA2 mAb (open histograms) and isotype control (shaded histograms). Representative of at least seven experiments.

Protein expression pattern of HHLA2: The expression of HHLA2 at the protein level is completely unknown at present. To examine the protein expression, a panel of monoclonal antibodies (mAbs) was generated against HHLA2 from mice as mice do not express the HHLA2 gene. The specificity of the mAbs was demonstrated by ELISA and FACS in which mAbs reacted with HHLA2 but not with other B7 molecules (FIG. 2A).

Using the anti-HHLA2 mAb clone 566.1, HHLA2 expression was examined on APCs by FACS. CD14 positive monocytes in human peripheral blood mononuclear cells (PBMCs) expressed significant levels of HHLA2 and the expression was further up-regulated by stimulation with LPS and IFN-γ (FIG. 2B). Resting CD19 positive B cells did not express HHLA2, but the expression was induced by LPS and IFN-γ stimulation (FIG. 2B). No clear HHLA2 protein could be detected on blood monocyte-derived immature dendritic cells (DCs) or LPS/IFN-γ-induced mature DCs (FIG. 2B). For T cells, both CD4 and CD8 T cells in PBMCs did not express HHLA2; both were still negative after stimulation with plate-bound anti-CD3 (FIG. 2B). As a control, PD-L1, another B7 molecule, was induced on monocytes, B cells and DCs after LPS/IFN-γ stimulation and was induced on CD4 and CD8 T cells after stimulation with anti-CD3 (FIG. 2B). Collectively, these results demonstrate that endogenous HHLA2 is an integral cell surface protein constitutively expressed on monocytes and induced on B cells.

Figures 3A, 3B, 3C:
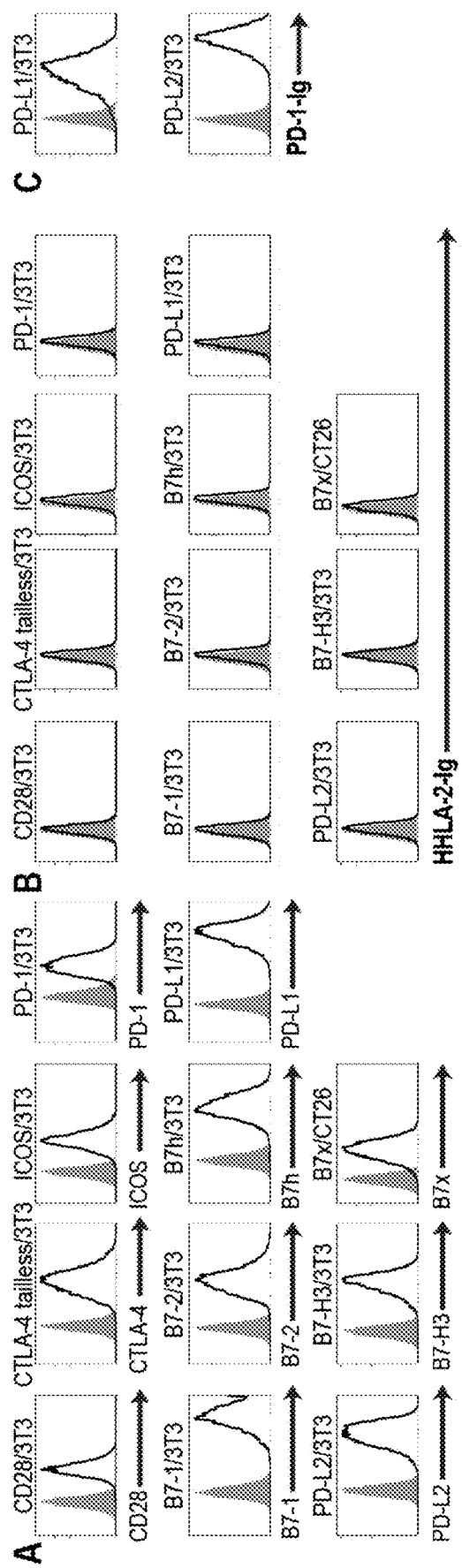
FIG. 3A-3C. HHLA2 does not bind other known members of the CD28 and B7 families. (A) 3T3 or CT26 cells were transfected with MSCV vectors to stably express cell-surface human CD28, CTLA-4 without cytoplasmic tail, ICOS, PD-1, B7-1, B7-2, B7h, PD-L1, PD-L2, B7-H3, and B7x. All transfectants were stained with specific mAbs (open histograms) or control Abs (shaded histograms). (B) Transfectants were stained with HHLA2-Ig fusion protein (open histograms) or control fusion proteins Ig or B7x-Ig (shaded histograms), and then stained with a PE-conjugate anti-human IgG Fc. (C) As positive controls, 3T3 cells expressing PD-L1 or PD-L2 were stained with PD-1-Ig (open histograms) or control Ig (shaded histograms).

HHLA2 does not bind other known members of the CD28 and B7 families: All previously characterized B7 family members can act as ligands and regulate T cell function by binding to receptors. The receptor for HHLA2 is unknown, therefore it was first asked whether any of the known CD28 family members are the receptor for HHLA2. To this end, an HHLA2-Ig fusion protein was generated consisting of the extracellular portion of human HHLA2 and the Fc portion of IgG1 and three other controls including B7x-Ig, B7-H3-Ig, and only the Fc portion of human IgG1 (Ig control). The HHLA2-Ig fusion protein and the controls, produced in the same system and purified in the same way, were used to search for the interactions between HHLA2 and the CD28 family members using FACS analysis. To do this 3T3 lines expressing cell surface human CD28, ICOS, PD-1 (FIG. 3A) were established. CTLA-4 is not primarily a cell surface protein (FIG. 1B), mainly due to the fact that it contains an intracellular localization motif (TTGVYVKMPPT) (SEQ ID NO:3) in its cytoplasmic tail (32). A 3T3 line expressing cell surface CTLA-4 was established which did not contain the cytoplasmic tail (FIG. 3A). In FACS experiments, HHLA2-Ig, like the other control Igs (Ig, B7x-Ig and B7-H3-Ig), did not bind CD28, CTLA-4, ICOS, and PD-1 on the cell surface of 3T3 cells (FIG. 3B). Within the B7 family, B7-1 can bind to another B7 molecule PD-L1 (21). To test whether HHLA2 binds to any of known B7 family members, 3T3 and CT26 lines were established that expressed cell surface human B7-1, B7-2, B7h, PD-L1, PD-L2, B7-H3 and B7x, and found that neither HHLA2-Ig nor B7x-Ig bound the other B7 molecules (FIG. 3B). As a positive control, PD-1-Ig bound 3T3 cells expressing PD-L1 or PD-L2 (FIG. 3C). These results reveal that neither the known members of the CD28 family nor those of the B7 family interact with HHLA2.

Figures 4A, 4B:
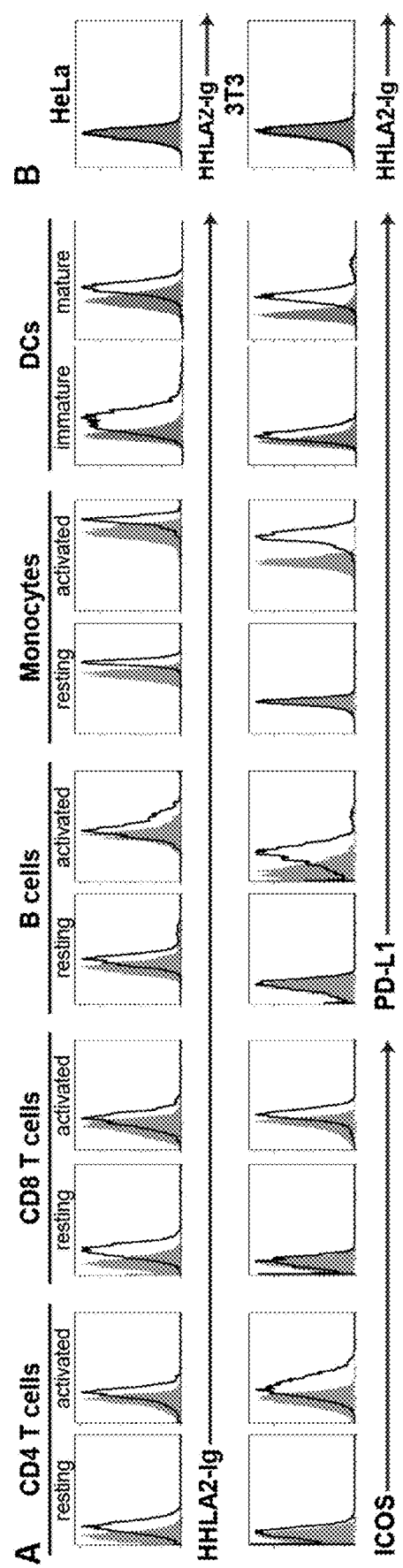
FIG. 4A-4B. T cells and other immune cells constitutively express a putative receptor for HHLA2. (A) T cells, B cells and monocytes from PBMCs and DCs derived from blood monocytes were stained with HHLA2-Ig fusion protein (open histograms) or control Ig (shaded histograms), and then stained with a PE-conjugate anti-human IgG Fc. CD4 and CD8 T cells were stimulated with anti-CD3 for three days, whereas B cells and monocytes were stimulated with LPS/IFN-γ for three days. Immature DCs were generated from blood monocytes and were induced with LPS/IFN-γ to be mature DCs. HHLA2 bound T cells, B cells, monocytes and DCs. ICOS was induced on activated CD4 and CD8 T cells, whereas PD-L1 was induced on APCs. (B) In contrast to these immune cells, HHLA2 bound neither human HeLa cells nor mouse 3T3 cells. HHLA2-Ig fusion protein (open histograms) and control Ig (shaded histograms). Representative of at least five experiments.

Constitutive expression of an HHLA2 putative receptor on T cells and other immune cells. T cells express receptors for members of the B7 family. To test whether T cells have an HHLA2 receptor, HHLA2-Ig was used and control Ig to stain T cells from PBMCs. FACS analyses showed that HHLA2 bound freshly isolated resting CD4 and CD8 T cells (FIG. 4A). After stimulation with plate-bound anti-CD3 for three days, activated CD4 and CD8 T cells still expressed a receptor for HHLA2 (FIG. 4A). In contrast, ICOS was not expressed on resting CD4 and CD8 T cells but was induced after stimulation (FIG. 4A). HHLA2 receptor positive cells and ICOS positive cells were partially overlapping. PD-1, another CD28 family member, was recently reported to be expressed on human B cells (33). It was therefore examined whether APCs have a receptor for HHLA2. HHLA2-Ig bound freshly isolated B cells and monocytes, suggesting these cells express a receptor for HHLA2 (FIG. 4A). PBMCs were further stimulated with LPS/IFN-γ for three days, and it was found B cells and monocytes were activated, as evidenced by induced expression of PD-L1. Both activated B cells and monocytes were stained by HHLA2-Ig (FIG. 4A), suggesting resting and activated B cells as well as monocytes have a putative HHLA receptor. Finally, dendritic cells (DCs) were examined. It was found that HHLA2 bound blood monocyte-derived immature DCs as well as LSP/IFN-γ-induced mature DCs (FIG. 4A). In contrast to immune cells, HHLA2 did not bind human HeLa cells and mouse 3T3 cells (FIG. 4B), suggesting these cells did not have an HHLA2 receptor. Taken together, these results indicate that a putative HHLA2 receptor is constitutively expressed on T cells, B cells, monocytes, and DCs.

Figures 5A, 5B, 5C:
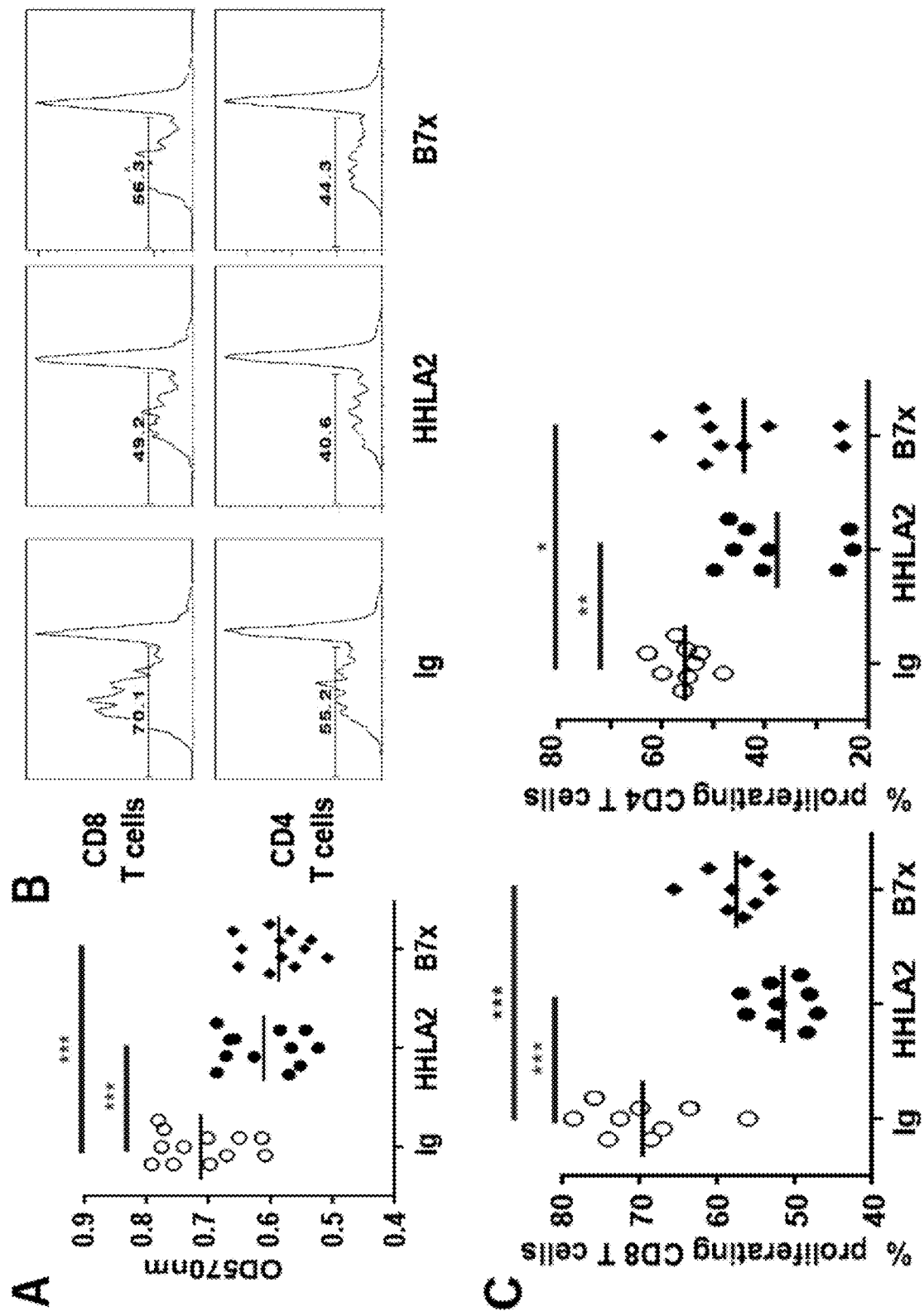
FIG. 5A-5C. Coinhibition of HHLA2 on TCR-mediated CD4 and CD8 T cell proliferation. (A) T cells purified from PBMCs were activated with a combination of plate-bound anti-CD3 and either plate-bound HHLA2-Ig (4 μg/ml), control Ig (4 μg/ml), or B7x-Ig (4 μg/ml) for three days. Metabolic activity was then determined by MTT assay. (B-C) CFSE-labeled T cells were stimulated with a combination of plate-bound anti-CD3 and either plate-bound HHLA2-Ig (10 μg/ml), control Ig (10 μg/ml), or B7x-Ig (10 μg/ml) for five days. T cells were then stained with anti-CD4 and anti-CD8, and analyzed by flow cytometry. Representative FACS plots showed CFSE dilution among CD4 and CD8 T cells (B). The percentages of proliferating CD4 and CD8 T cells were calculated by CFSE dilution (C). N=9-12, *P<0.05; P<0.01, *P<0.001

HHLA2 inhibits TCR-mediated CD4 and CD8 T cell proliferation: Based on the data showing that HHLA2 protein was detected on APCs and a putative receptor was constitutively expressed on T cells, it was examined whether HHLA2 was able to regulate T cell function using a system modified from previous studies (23). In this system, purified T cells were activated with plate-bound mAb to human CD3 and the activation of T cells was determined on day three and five. Firstly a dose titration was performed of anti-CD3 and it was found that T cells from different normal donors needed different concentrations of anti-CD3 to achieve the middle level of proliferation. Therefore, different suitable concentrations of anti-CD3 were used for T cell experiments. The MTT assay was used to quantify anti-CD3 induced T cell activation in the presence of immobilized HHLA2-Ig, control Ig, or B7x-Ig (FIG. 5A). HHLA2-Ig significantly decreased T cell activation induced by anti-CD3 (FIG. 5A). As a control, B7x-Ig also inhibited T cell activation in the same system (23). As both CD4 and CD8 T cells constitutively express an HHLA2 receptor, it was next examined whether HHLA2 was able to inhibit both CD4 and CD8 T cells. Purified T cells from PBMCs were labeled with carboxyfluorescein diacetate succinimidyl ester (CF SE), and stimulated with anti-CD3 in the presence of immobilized HHLA2-Ig, control Ig, or B7x-Ig for five days. These cells were then analyzed by FACS with anti-CD4 and anti-CD8. HHLA2-mediated inhibition was determined by gating on CD4 and CD8 T cell populations and measuring CFSE fluorescence intensity. Both CD4 and CD8 T cells proliferated vigorously when incubated with anti-CD3 and control Ig (FIGS. 5B,C), with more than 55% of CD4 and 69% of CD8 T cells dividing. However, when T cells were incubated with anti-CD3 and HHLA2-Ig, significantly fewer CD4 and CD8 T cells proliferated, with less than 38% of CD4 and 52% of CD8 T cells dividing (FIGS. 5B,C). Similarly, B7x-Ig also inhibited both CD4 and CD8 T cell proliferation, with less than 44% of CD4 and 57% of CD8 T cells dividing (FIG. 5). These findings from two functional assays demonstrate that HHLA2 inhibits TCR-mediated proliferation of both human CD4 and CD8 T cells.

Figure 6:
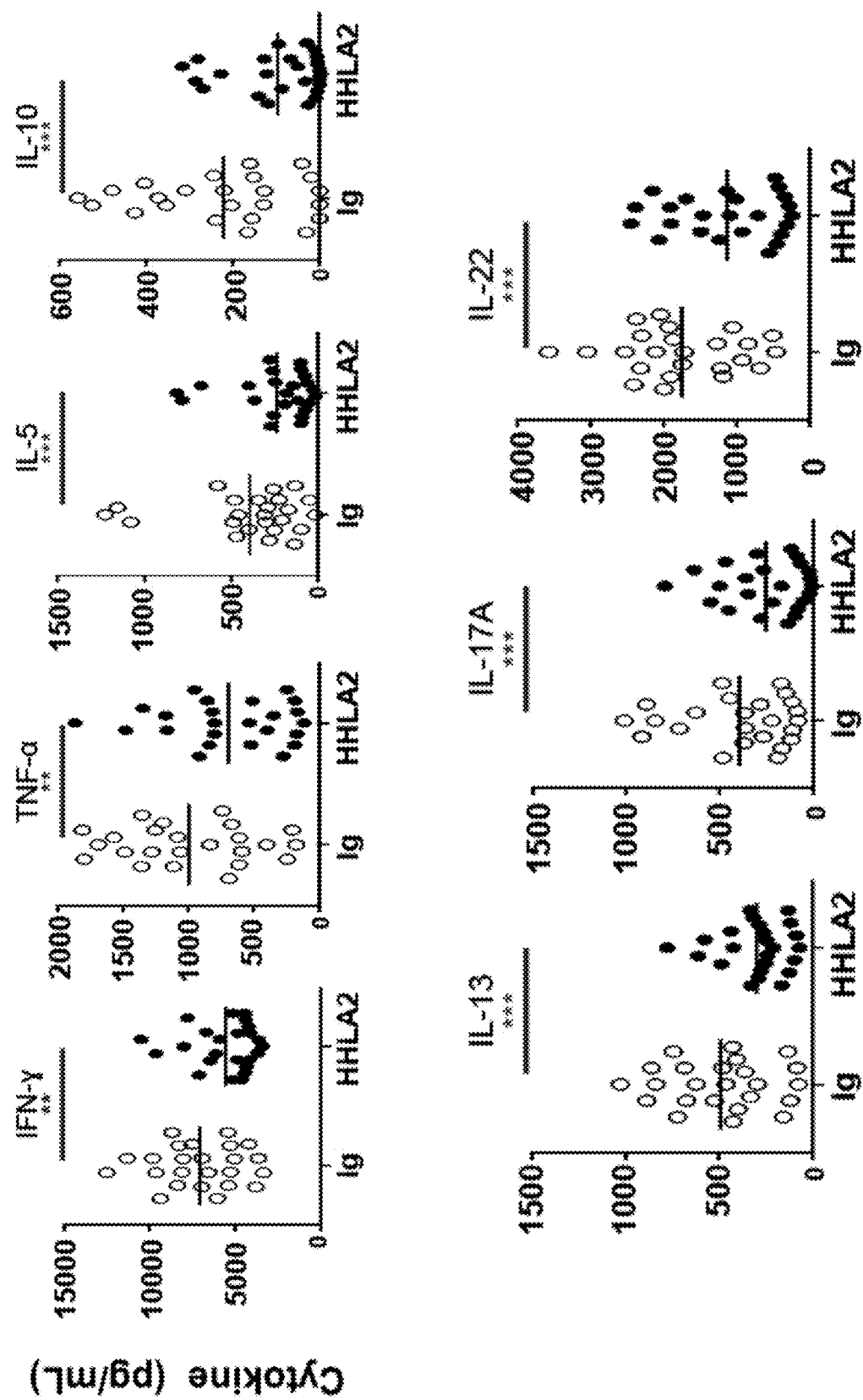
FIG. 6. Inhibition of HHLA2 on cytokine production from T cells. Purified T cells were stimulated with a combination of plate-bound anti-CD3 and either plate-bound HHLA2-Ig (4 μg/ml) or control Ig (4 μg/ml) for three days. The cytokine levels of the supernatants were measured using Th1/Th2/Th9/Th17/Th22 flowcytomix. HHLA2 significantly reduced production of seven cytokines from T cells including IFN-γ, TNF-α, IL-5, IL-10, IL-13, IL-17A, and IL-22. N=24, P<0.01, *P<0.001

HHLA2 inhibits cytokine production from T cells: Next tested was the effect of HHLA2 on cytokine production from T cells. Purified T cells from PBMCs were stimulated with anti-CD3 in the presence of immobilized HHLA2-Ig or control Ig for three days and cytokines in the supernatants were measured using Th1/Th2/Th9/Th17/Th22 flowcytomix. Among the 13 T cell-derived cytokines tested, it was found HHLA2 significantly reduced production of 7 cytokines from T cells: IFN-γ (21% reduction), TNF-α (30% reduction), IL-5 (39% reduction), IL-10 (56% reduction), IL-13 (39% reduction), IL-17A (36% reduction), and IL-22 (35% reduction) (FIG. 6). HHLA2 reduced production of IL-2 and IL-9, but the differences did not reach statistical significance. In addition, there was no effect of HHLA2 on cytokine production of IL-113, IL-4, IL-6, and IL-12p70. These results suggest that HHLA2 is able to suppress certain cytokines produced from T cells induced by TCR signaling.

HHLA2 protein has limited expression in normal tissues: Using monoclonal antibodies to HHLA, an immunohistochemistry (IHC) protocol was developed to evaluate HHLA2 protein expression in normal human organs and common cancers. It was found that HHLA2 protein was in the epithelium of the gut, breast, placenta, and gallbladder, but not in other organs such as skin, liver, uterine cervix, subcutis, prostate, pancreas, spleen, tonsils, umbilical cord, lymph node, esophagus, adrenal, ovary, stomach, thyroid, lung, thymus, larynx, brain, aorta, uterus, and salivary glands (Table 1).

Figure 7:
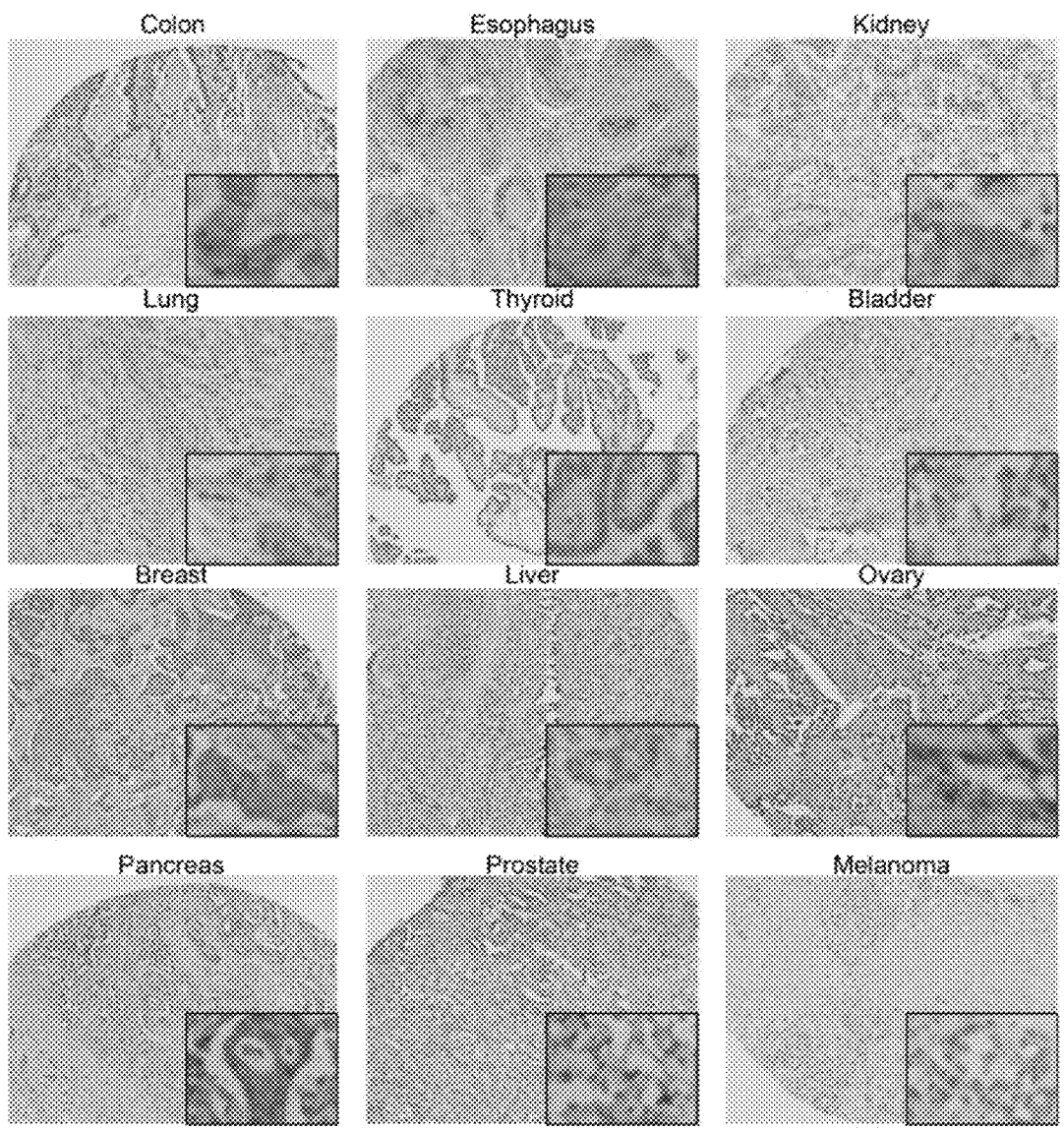
FIG. 7: Immunohistochemistry results showing HHLA2 is over-expressed in 50% or more of the cancerous lung, thyroid, breast, ovary, pancreas, and melanoma samples and is also expressed in other cancerous esophagus, kidney, liver, bladder, and prostate.

HHLA2 protein is over-expressed in many human cancers: Using IHC, it was found that HHLA2 was over-expressed in 50% or more of the cancerous lung, thyroid, breast, ovary, pancreas, and melanoma samples (Table 2 and FIG. 7). HHLA2 was also expressed in other cancerous esophagus, kidney, liver, bladder, and prostate (Table 2 and FIG. 7). In addition, some hematological malignancies were found including lymphoma and leukemia expressed HHLA2 on their surface by flow cytometry (Table 3).

TABLE 1

IHC staining for HHLA2 protein in normal human organs.
Normal Tissues (Number Positive/Total Cores Analyzed)

| | | |
|---|---|---|
| Skin (0/2) | Liver (0/2) | Uterine Cervix (0/4) |
| Subcutis (0/2) | Gallbladder (5/11) | Prostate (0/2) |
| Breast (2/2) | Pancreas (0/2) | Placenta (2/2) |
| Spleen (0/2) | Tonsils (0/2) | Umbilical Cord (0/2) |
| Lymph Node (0/12) | Esophagus (0/2) | Adrenal (0/2) |
| Ovary (0/1) | Stomach (0/2) | Thyroid (0/2) |
| Lung (0/2) | Small Intestine (2/2) | Thymus (0/2) |
| Larynx (0/9) | Colon (2/2) | Brain (0/6) |
| Aorta (0/2) | Kidney (3/4) | Uterus (0/9) |
| Salivary Glands (0/2) | | |

TABLE 2

IHC staining for HHLA2 protein in human common cancers from various organs.
Cancer Samples (Number Positive/Total Cores)

| | | |
|---|---|---|
| Stomach (0/10) | Breast (7/10) | Endometrial (0/9) |
| Esophagus (2/10) | Liver (4/10) | Gallbladder (0/10) |
| Lung (6/9) | Bladder (4/10) | Larynx (0/10) |
| Colon/Rectum (3/8) | Ovary (4/8) | Uterine Cervix (0/10) |
| Thyroid (6/9) | Pancreas (5/10) | Lymphoma (0/10) |
| Kidney (2/6) | Prostate (3/9) | Malignant Melanoma (5/9) |

TABLE 3

Expression of HHLA2 protein in various human cancer cell lines determined by flow cytometry.

| Human Cell Lines | Derived From | HHLA2 Expression |
|---|---|---|
| U937 | Histiocytic Lymphoma | + |
| Raji | Burkitt lymphoma | + |
| HL60 | Acute Promyelocytic Leukemia | + |
| MOLM13 | Acute monocytic leukemia | + |
| K562 | Chronic myelogenous leukemia | + |
| CEM | Acute lymphoblastic leukemia | + |
| SK-BR-5 | Breast carcinoma (Metastasis) | + |
| HCC-1143 | Breast ductal carcinoma | + |
| MDA-MB-231 | Breast adenocarcinoma | + |
| BT-20 | Breast carcinoma | + |
| BT-549 | Breast ductal carcinoma | + |
| SK-BR-7 | Breast carcinoma | − |
| SK-LC-1 | Lung adenocarcinoma | − |
| SK-LC-7 | Lung adenocarcinoma | − |
| SK-OV-6 | Ovarian carcinoma | − |
| Hela | Cervical cancer | − |
| Jurkat | Acute T cell leukemia | − |
| THP-1 | Acute monocytic leukemia | − |
| KG1 | Acute myelogenous leukemia | − |

Discussion

Herein is provided evidence for HHLA2 as a new member of the B7 family that inhibits proliferation and cytokine production of both human CD4 and CD8 T cells. This is significant and unexpected in light of previous reports of methods of using pHHLA2 to co-stimulate T-cells (see US Patent Application Publication 20090175876). HHLA2 was originally cloned as a gene that was polyadenylated within a long terminal repeat (LTR) of the HERV-H endogenous retrovirus family (29), exhibiting homology with B7 (29, 30). It was found that HHLA2 has all the characteristics of a B7 family member. Similar to other members of the B7 family, HHLA2 shares 10-18% of amino acid identity and 23-33% of similarity to other human B7 molecules. It is already demonstrated that the IgV domain is the receptor-binding domain for B7-1 (34), B7-2 (35), PD-L1 (36) and PD-L2 (37). Like other B7s, HHLA2 has extracellular IgV and IgC domains. With the phylogenetic analyses, it was found that HHLA2 formed the third group with B7x and B7-H3 within the B7 family. Indeed, the highest homology sequences to HHLA2 are B7-H3 and B7x. The bioinformatic analyses and other results (29, 30) reveal that HHLA2 is found in various species including human, monkey, frog, and fish, but is not expressed in mouse and rat. Mouse and rat have only HHLA2 pseudogenes (30). This is unique as all other known members of the B7 family and of the CD28 family are found in both human and mouse.

Compared to other B7s, human HHLA2 has a different expression pattern. HHLA2 protein was expressed highly and constitutively on monocytes, while its expression on human B cells was induced by inflammatory stimulation. However, blood monocyte-derived DCs and T cells were HHLA2 negative even after activation with LPS/IFN-γ and anti-CD3, respectively. Differently from HHLA2, it was found that the other B7 molecule, PD-L1, was not expressed in human resting T cells and APCs but was induced on these immune cells after activation. B7-2 is expressed at very low levels on human resting B cells and immature DCs and is induced to high levels with stimuli (38, 39), while B7x is hardly detected on normal human T cells and APCs (38). These studies highlight the dramatic differences in the spatial and temporal expression of the individual members of the B7 family.

HHLA2 appears to have a counter-receptor that is distinct from CD28, CTLA-4, ICOS, PD-1 and all B7 molecules. CD28 is constitutively expressed on T cells, whereas CTLA-4, ICOS, and PD-1 are induced after T cell activation (1-3). HHLA2-Ig fusion protein did not interact with any known members of the CD28 and B7 families, demonstrating that these molecules are not the receptor for HHLA2. These results are consistent with the phylogenetic analyses which suggests the receptors for the group III (HHLA2, B7x, and B7-H3) may be distinct from the receptors for groups I and II. Interestingly, HHLA2 bound not only to activated human CD4 and CD8 T cells but also to resting CD4 and CD8 T cells. Therefore, HHLA2 joins B7-1 and B7-2 to recognize receptors expressed on both resting and activated T cells.

HHLA2 is able to function as a negative regulator of human T cells: In the presence of TCR signaling, immobilized HHLA2 protein suppressed proliferation of both human CD4 and CD8 T cells as effectively as B7x in the same experimental system. The second line of evidence that supported an inhibitory role for HHLA2 in T cell regulation is its effect on cytokine production. Among 13 cytokines from T cells induced by TCR signaling, HHLA2 significantly reduced the production of 7 cytokines including IFN-γ, TNF-α, IL-5, IL-10, IL-13, IL-17A, and IL-22, indicating that HHLA2 is able to inhibit T cell cytokine production. It was found that human T cells from different donors had considerable variation in cytokine production, which may reflect an interesting heterogeneity in the human response. In the group III of the B7 family, B7x suppresses T cells and is widely over-expressed in many human solid tumors; B7-H3 is reported to have costimulatory and coinhibitory effects (26), although clinical observations suggest that it functions in tumor immune evasion. This group is now expanded to include HHLA2 as a T cell coinhibitor. In addition to T cells, human APCs also express a receptor for HHLA2.

In summary, herein is characterized a member of the B7 family that serves as an attenuator of T cell responses. It is the first B7 family member identified to exist in humans but not in mice. Its putative receptor is constitutively expressed on human T cells and APCs. The expression patterns of HHLA2 and its putative counter-receptor coupled with its coinhibitory function suggests that this pathway is a potent regulator of human immune responses at both the very early and late stages. Notably, in the clinic, CTLA-4-Ig fusion proteins (Abatacept and Belatacept) inhibit T cell functions and have already been used to treat adult rheumatoid arthritis and to prevent acute kidney transplant rejection (40, 41), respectively, a mAb blocking CTLA-4 functions (Ipilimumab) was recently approved for treatment of metastatic melanoma (42, 43) and some mAbs against PD-1 and PD-L1 are currently in clinical trials with cancer patients (44, 45). Similarly, the newly-identified inhibitory HHLA2 pathway permits new therapies for human cancers, autoimmune disorders, infection, and transplant rejection.

The HHLA2 expression results in normal and cancerous tissues indicate that targeting HHLA2 can be a way to deliver drugs and antibodies to cancers. For example, molecules which can bind HHLA2 protein, such as anti-HHLA2 antibody or antibody-drug conjugate (ADC) and HHLA2 receptors or receptor-drug conjugates, can be used to treat human cancers which express HHLA2. In addition, HHLA2 expression can be used as a diagnostic marker for many cancers. Because most normal tissues do not express HHLA2, but most human cancer do express HHLA2, then HHLA2 expression can be used as a diagnostic marker for many cancers.

Materials and Methods

Bioinformatic analysis. BLAST was used to search public databases with protein sequences. Sequence alignment and homology comparison were done with MacVector 10.6. The phylogenetic tree was generated by PAUP (4.0b10) using sequence alignment by removal of significant inserts and trimming C- and N-terminal extensions (31). Motifs and domains were analyzed with EMBL-EBI tools, SMART, and CBS Prediction.

Mice and cells. BALB/c mice were purchased from the National Cancer Institute and maintained under specific pathogen-free conditions. Human PBMCs were isolated by Ficoll-Hypaque gradient centrifugation. All protocols were reviewed and approved by the Albert Einstein College of Medicine Institutional Animal Care and Use Committee and Institutional Review Board. Cell lines were cultured in complete DMEM or RPMI1640 media.

Production and purification of fusion proteins. HHLA2-Ig and B7x-Ig proteins were prepared by fusing the coding region of the extracellular domain without signal peptide of human HHLA2 or B7x to a human IgG1 Fc tag of plasmid pMT/BiP V2 as described (23). The pMT/BiP V2 construct itself produced human IgG1 Fc tag as a control. All constructs were co-transfected into *Drosophila* cell line S2 with a hygromycin resistance plasmid, and the stable transfected cell lines were induced to secrete fusion proteins in Express Five serum-free medium (LifeTechnologies). Proteins were purified on Protein G Plus Agarose columns (Pierce) and then FPLC. The purity and identity of fusion proteins were confirmed by SDS-PAGE, Western blotting, and protein sequencing with MALDI-TOF-MS/MS.

Retrovirus constructs and cell line transfectants. HHLA2-YFP fusion protein construct was generated by using PCR to amplify the coding sequence of HHLA2 without the stop codon and then cloned into the Bgl II site of the L50-YFP/MSCV vector. CTLA-4 in L50-FYP/MSCV vector was reported previously (46). The coding sequences of human CD28, PD-1, ICOS, B7-1, B7-2, B7h, PD-L1, PD-L2, B7-H3, and B7x were cloned into XhoI/NotI or XhoI/EcoRI sites of MSCV vector. The coding sequence of human CTLA-4 without a cytoplasmic tail was cloned into an MSCV vector as well. All vectors were used to generate retrovirus and then transfected into cell lines 3T3 or CT26 cell lines. Positive cell line transfectants were sorted out by FACS using specific mAbs or YFP as a marker.

Generation of monoclonal antibodies to human HHLA2. Hybridomas producing mAbs to human HHLA2 were generated by standard techniques from splenocytes of HHLA2-Ig-immunized BALB/c mice fused to NSO myeloma cells. Four independent clones, 566.1 (IgG1), 351.7 (IgG1), 457.23 (IgG1), and 205.1 (IgG1) were selected by ELISA as their mAbs recognized HHLA2-Ig, but not controls including B7x-Ig, B7-H3-Ig, and normal human IgG. After this preliminary screening, specificity of mAbs were further determined by FACS positive staining of a 3T3 transfectant expressing HHLA2-YFP but negative staining of transfectants expressing other human B7s (B7-1, B7-2, B7g, PD-L1, PD-L2, B7-H3, and B7x) and human CD28 family members (CD28, CTLA-4, ICOS, and PD-1). mAbs were purified by Protein G Plus Agarose columns and biotinylated with EZ-Link Sulfo-NHS-Biotin kit (Thermo Scientific).

Antibodies and flow cytometry. Cells were incubated with Fc blocking reagents and then stained with combinations of the following anti-human antibodies: CD152-PE, CD28-PE, B7-1-PE, B7-2-PE, PD-1-PE, PD-L1-PE, PD-L2-PE, ICOS-PE, ICOSL-PE, B7H4-PE, CD14-FITC, CD19-FITC, CD8a-Percp-Cy5.5, CD4-APC, CD83-APC, streptavidin and isotype controls (eBioscience). Biotinylated anti-hB7-H3 was purchased from R&D. For receptor binding, cells were incubated with HHLA2-Ig, B7x-Ig, or control Ig for 45 min on ice and then stained with PE-anti-human IgG Fc (Jackson Immunoresearch). Samples were acquired on a FACSCalibur, LSRII or LSRII yellow (BD Biosciences), and analyzed with FlowJo (Treestar).

Human antigen-presenting cells and activation. Human CD19+ B cells and CD14+ monocytes in PBMCs were activated as previously described (38). B cells were activated by IFN-γ (100 ng/ml, eBioscience) and LPS (60 µg/ml, sigma) for three day, and monocytes were stimulated by IFN-γ (100 ng/ml) and LPS (100 ng/ml) for three days. DCs were generated from human blood monocytes (47). Monocytes from PBMCs were incubated with completed RPMI1640 containing 10% human serum AB (Atlanta Biological), human GM-CSF (100 ng/ml, R&D) and human IL-4 (50 ng/ml) for six days to generate immature DCs. These immature DCs were further stimulated with LPS (1 µm/ml) and IFN-γ (100 ng/ml) for two days to generate mature DCs.

Human T cell coinhibition assay. Human T cells were purified from PBMCs with CD2 Microbeads (Miltenyi Biotec) and incubated ($2 \times 10^5$/well) with different concentrations (0.1-10 µg/ml) of plate-bound anti-CD3 (OKT3, eBioscience) for three days. The T cell proliferation was determined by MTT assay and plates were read at 570 nm. T cells from different donors needed different concentrations of anti-CD3 to achieve the middle level of proliferation. After determining the suitable anti-CD3 concentration for each donor T cells, 96-well flat-bottom plates were pre-coated with anti-CD3, HHLA-2-Ig, control Ig, or B7x-Ig in PBS at 4° C. overnight. Wells were washed and incubated with purified T cells for three days. T cell proliferation was then measured with MTT assay. For the CFSE (Sigma) labeled proliferation assay, CFSE-labeled human T cells were incubated with plate-bound anti-CD3, HHLA-2-Ig, control Ig, or B7x-Ig for five days, and stained with anti-CD4 and anti-CD8 for flow cytometry.

Cytokine analysis. Aliquots of supernatants were collected at 70 h after initiation of T cell cultures. Th1/Th2/Th9/Th17/Th22 13plex FlowCytomix Multiplex (eBioscience) was used for the measurement of human IFN-γ, IL-1β, IL-2, IL-4, IL-5, IL-6, IL-9, IL-10, IL-12 p70, IL-13, IL-17A, IL-22, and TNF-α according to the manufacturer's instructions.

Confocal microscopy. Cells were seeded on glass bottom microwell dishes (MatTek Corp.) for 48 h and then were observed by using Leica SP2 confocal microscopy.

Statistics. Statistical significance was calculated with the paired- or unpaired t-test using Prism software version 4.0b (GraphPad). A p value of <0.05 was considered statistically significant.

REFERENCES

1. Chen L (2004) Co-inhibitory molecules of the B7-CD28 family in the control of T-cell immunity. *Nat Rev Immunol* 4(5):336-347.
2. Greenwald R J, Freeman G J, & Sharpe A H (2005) The B7 family revisited. *Annu Rev Immunol* 23:515-548.
3. Zang X & Allison J P (2007) The B7 family and cancer therapy: costimulation and coinhibition. *Clin Cancer Res* 13(18 Pt 1):5271-5279.
4. Swallow M M, Wallin J J, & Sha W C (1999) B7h, a novel costimulatory homolog of B7.1 and B7.2, is induced by TNFalpha. *Immunity* 11(4):423-432.

5. Yoshinaga S K, et al. (1999) T-cell co-stimulation through B7RP-1 and ICOS. *Nature* 402(6763): 827-832.
6. Ling V, et al. (2000) Cutting edge: identification of GL50, a novel B7-like protein that functionally binds to ICOS receptor. *J Immunol* 164(4):1653-1657.
7. Wang S, et al. (2000) Costimulation of T cells by B7-H2, a B7-like molecule that binds ICOS. *Blood* 96(8):2808-2813.
8. Brodie D, et al. (2000) LICOS, a primordial costimulatory ligand? *Curr Biol* 10(6):333-336.
9. Hutloff A, et al. (1999) ICOS is an inducible T-cell co-stimulator structurally and functionally related to CD28. *Nature* 397(6716):263-266.
10. Parry R V, Rumbley C A, Vandenberghe L H, June C H, & Riley J L (2003) CD28 and inducible costimulatory protein Src homology 2 binding domains show distinct regulation of phosphatidylinositol 3-kinase, Bcl-xL, and IL-2 expression in primary human CD4 T lymphocytes. *J Immunol* 171(1):166-174.
11. Zang X, et al. (2006) A genetic library screen for signaling proteins that interact with phosphorylated T cell costimulatory receptors. *Genomics* 88(6):841-845.
12. Crotty S (2011) Follicular helper CD4 T cells (TFH). *Annu Rev Immunol* 29:621-663.
13. Yong P F, Salzer U, & Grimbacher B (2009) The role of costimulation in antibody deficiencies: ICOS and common variable immunodeficiency. *Immunol Rev* 229(1): 101-113.
14. Yao S, et al. (2011) B7-h2 is a costimulatory ligand for CD28 in human. *Immunity* 34(5):729-740.
15. Freeman G J, et al. (2000) Engagement of the PD-1 immunoinhibitory receptor by a novel B7 family member leads to negative regulation of lymphocyte activation. *J Exp Med* 192(7):1027-1034.
16. Dong H, Zhu G, Tamada K, & Chen L (1999) B7-H1, a third member of the B7 family, co-stimulates T-cell proliferation and interleukin-10 secretion. *Nat Med* 5(12): 1365-1369.
17. Latchman Y, et al. (2001) PD-L2 is a second ligand for PD-1 and inhibits T cell activation. *Nat Immunol* 2(3): 261-268.
18. Tseng S Y, et al. (2001) B7-DC, a new dendritic cell molecule with potent costimulatory properties for T cells. *J Exp Med* 193(7):839-846.
19. Okazaki T & Honjo T (2007) PD-1 and PD-1 ligands: from discovery to clinical application. *Int Immunol* 19(7): 813-824.
20. Hofmeyer K A, Jeon H, & Zang X (2011) The PD-1/PD-L1 (B7-H1) pathway in chronic infection-induced cytotoxic T lymphocyte exhaustion. *J Biomed Biotechnol* 2011:451694.
21. Butte M J, Keir M E, Phamduy T B, Sharpe A H, & Freeman G J (2007) Programmed death-1 ligand 1 interacts specifically with the B7-1 costimulatory molecule to inhibit T cell responses. *Immunity* 27(1):111-122.
22. Chapoval A I, et al. (2001) B7-H3: a costimulatory molecule for T cell activation and IFN-gamma production. *Nat Immunol* 2(3):269-274.
23. Zang X, et al. (2003) B7x: a widely expressed B7 family member that inhibits T cell activation. *Proc Natl Acad Sci USA* 100(18):10388-10392.
24. Sica G L, et al. (2003) B7-H4, a molecule of the B7 family, negatively regulates T cell immunity. *Immunity* 18(6):849-861.
25. Prasad D V, Richards S, Mai X M, & Dong C (2003) B7S1, a novel B7 family member that negatively regulates T cell activation. *Immunity* 18(6):863-873.
26. Hofmeyer K A, Ray A, & Zang X (2008) The contrasting role of B7-H3. *Proc Natl Acad Sci USA* 105(30):10277-10278.
27. Abadi Y M, et al. (2013) Host B7x promotes pulmonary metastasis of breast cancer. *J Immunol* 190(7):in press.
28. Barach Y S, Lee J S, & Zang X (2011) T cell coinhibition in prostate cancer: new immune evasion pathways and emerging therapeutics. *Trends Mol Med* 17(1):47-55.
29. Mager D L, Hunter D G, Schertzer M, & Freeman J D (1999) Endogenous retroviruses provide the primary polyadenylation signal for two new human genes (HHLA2 and HHLA3). *Genomics* 59(3):255-263.
30. Flajnik M F, Tlapakova T, Criscitiello M F, Krylov V, & Ohta Y (2012) Evolution of the B7 family: co-evolution of B7H6 and NKp30, identification of a new B7 family member, B7H7, and of B7's historical relationship with the MEW. *Immunogenetics* 64(8):571-590.
31. Swofford D L (2000) PAUP. Phylogenetic Analysis Using Parsimony (and other methods). Version 4. Sinauer Associates, Sunderland, Mass.
32. Leung H T, Bradshaw J, Cleaveland J S, & Linsley P S (1995) Cytotoxic T lymphocyte-associated molecule-4, a high-avidity receptor for CD80 and CD86, contains an intracellular localization motif in its cytoplasmic tail. *J Biol Chem* 270(42):25107-25114.
33. Thibult M L, et al. (2013) PD-1 is a novel regulator of human B-cells activation. *Int Immunol* 25(2):129-137.
34. Stamper C C, et al. (2001) Crystal structure of the B7-1/CTLA-4 complex that inhibits human immune responses. *Nature* 410(6828):608-611.
35. Schwartz J C, Zhang X, Fedorov A A, Nathenson S G, & Almo S C (2001) Structural basis for co-stimulation by the human CTLA-4/B7-2 complex. *Nature* 410(6828): 604-608.
36. Lin D Y, et al. (2008) The PD-1/PD-L1 complex resembles the antigen-binding Fv domains of antibodies and T cell receptors. *Proc Natl Acad Sci USA* 105(8): 3011-3016.
37. Lazar-Molnar E, et al. (2008) Crystal structure of the complex between programmed death-1 (PD-1) and its ligand PD-L2. *Proc Natl Acad Sci USA* 105(30):10483-10488.
38. Lee J S, et al. (2012) B7x in the periphery abrogates pancreas-specific damage mediated by self-reactive CD8 T cells. *J Immunol* 189(8):4165-4174.
39. Azuma M, et al. (1993) B70 antigen is a second ligand for CTLA-4 and CD28. *Nature* 366(6450):76-79.
40. Vincenti F, Dritselis A, & Kirkpatrick P (2011) Belatacept. *Nat Rev Drug Discov* 10(9):655-656.
41. Fiocco U, et al. (2008) Co-stimulatory modulation in rheumatoid arthritis: the role of (CTLA4-Ig) abatacept. *Autoimmun Rev* 8(1):76-82.
42. Sharma P, Wagner K, Wolchok J D, & Allison J P (2011) Novel cancer immunotherapy agents with survival benefit: recent successes and next steps. *Nat Rev Cancer* 11(11):805-812.
43. Hodi F S, et al. (2010) Improved survival with ipilimumab in patients with metastatic melanoma. *N Engl J Med* 363(8): 711-723.

44. Topalian S L, et al. (2012) Safety, activity, and immune correlates of anti-PD-1 antibody in cancer. *N Engl J Med* 366(26):2443-2454.

45. Brahmer J R, et al. (2012) Safety and activity of anti-PD-L1 antibody in patients with advanced cancer. *N Engl J Med* 366(26):2455-2465.

46. Pentcheva-Hoang T, Egen J G, Wojnoonski K, & Allison J P (2004) B7-1 and B7-2 selectively recruit CTLA-4 and CD28 to the immunological synapse. *Immunity* 21(3): 401-413.

47. O'Neill D W & Bhardwaj N (2005) Differentiation of peripheral blood monocytes into dendritic cells. *Curr Protoc Immunol* Chapter 22:Unit 22F 24.

What is claimed is:

1. A method of attenuating HHLA2 inhibition of a CD4 T cell proliferation or of a CD8 T cell proliferation or of a T cell cytokine production in a subject comprising administering an anti-HHLA2 antibody, or HHLA2-binding fragment thereof, to the subject.

2. The method of claim 1, wherein the CD4 T cell proliferation or the CD8 T cell proliferation is TCR-mediated.

3. The method of claim 1, wherein HHLA2 inhibition of the CD4 T cell proliferation is attenuated or inhibited.

4. The method of claim 1, wherein HHLA2 inhibition of the CD8 T cell proliferation is attenuated or inhibited.

5. The method of claim 1, wherein HHLA2 inhibition of the T cell cytokine production is attenuated or inhibited.

6. The method of claim 1, wherein the HHLA2 is a human HHLA2 protein.

7. The method of claim 6, wherein the HHLA2 protein comprises consecutive amino acid residues having the sequence set forth in SEQ ID NO:1.

8. The method of claim 1, wherein the antibody is a humanized antibody, a chimeric antibody or an isolated human antibody.

9. The method of claim 1, wherein the antibody is a monoclonal antibody.

10. The method of claim 1, wherein the anti-HHLA2 antibody or HHLA2-binding fragment is conjugated to a cytotoxic agent, an anti-cancer drug or a chemotherapeutic agent.

* * * * *

SEQUENCE LISTING

```
<160> NUMBER OF SEQ ID NOS: 4

<210> SEQ ID NO 1
<211> LENGTH: 414
<212> TYPE: PRT
<213> ORGANISM: HUMAN

<400> SEQUENCE: 1

Met Lys Ala Gln Thr Ala Leu Ser Phe Phe Leu Ile Leu Ile Thr Ser
1               5                   10                  15

Leu Ser Gly Ser Gln Gly Ile Phe Pro Leu Ala Phe Phe Ile Tyr Val
            20                  25                  30

Pro Met Asn Glu Gln Ile Val Ile Gly Arg Leu Asp Glu Asp Ile Ile
        35                  40                  45

Leu Pro Ser Ser Phe Glu Arg Gly Ser Glu Val Val Ile His Trp Lys
    50                  55                  60

Tyr Gln Asp Ser Tyr Lys Val His Ser Tyr Tyr Lys Gly Ser Asp His
65                  70                  75                  80

Leu Glu Ser Gln Asp Pro Arg Tyr Ala Asn Arg Thr Ser Leu Phe Tyr
                85                  90                  95

Asn Glu Ile Gln Asn Gly Asn Ala Ser Leu Phe Phe Arg Arg Val Ser
            100                 105                 110

Leu Leu Asp Glu Gly Ile Tyr Thr Cys Tyr Val Gly Thr Ala Ile Gln
        115                 120                 125

Val Ile Thr Asn Lys Val Val Leu Lys Val Gly Val Phe Leu Thr Pro
    130                 135                 140

Val Met Lys Tyr Glu Lys Arg Asn Thr Asn Ser Phe Leu Ile Cys Ser
145                 150                 155                 160

Val Leu Ser Val Tyr Pro Arg Pro Ile Ile Thr Trp Lys Met Asp Asn
                165                 170                 175

Thr Pro Ile Ser Glu Asn Asn Met Glu Glu Thr Gly Ser Leu Asp Ser
            180                 185                 190

Phe Ser Ile Asn Ser Pro Leu Asn Ile Thr Gly Ser Asn Ser Ser Tyr
        195                 200                 205

Glu Cys Thr Ile Glu Asn Ser Leu Leu Lys Gln Thr Trp Thr Gly Arg
    210                 215                 220

Trp Thr Met Lys Asp Gly Leu His Lys Met Gln Ser Glu His Val Ser
225                 230                 235                 240

Leu Ser Cys Gln Pro Val Asn Asp Tyr Phe Ser Pro Asn Gln Asp Phe
                245                 250                 255

Lys Val Thr Trp Ser Arg Met Lys Ser Gly Thr Phe Ser Val Leu Ala
            260                 265                 270

Tyr Tyr Leu Ser Ser Ser Gln Asn Thr Ile Ile Asn Glu Ser Arg Phe
        275                 280                 285

Ser Trp Asn Lys Glu Leu Ile Asn Gln Ser Asp Phe Ser Met Asn Leu
    290                 295                 300

Met Asp Leu Asn Leu Ser Asp Ser Gly Glu Tyr Leu Cys Asn Ile Ser
305                 310                 315                 320
```

```
Ser Asp Glu Tyr Thr Leu Leu Thr Ile His Thr Val His Val Glu Pro
            325                 330                 335

Ser Gln Glu Thr Ala Ser His Asn Lys Gly Leu Trp Ile Leu Val Pro
            340                 345                 350

Ser Ala Ile Leu Ala Ala Phe Leu Leu Ile Trp Ser Val Lys Cys Cys
            355                 360                 365

Arg Ala Gln Leu Glu Ala Arg Arg Ser Arg His Pro Ala Asp Gly Ala
            370                 375                 380

Gln Gln Glu Arg Cys Cys Val Pro Pro Gly Glu Arg Cys Pro Ser Ala
385                 390                 395                 400

Pro Asp Asn Gly Glu Glu Asn Val Pro Leu Ser Gly Lys Val
            405                 410

<210> SEQ ID NO 2
<211> LENGTH: 560
<212> TYPE: PRT
<213> ORGANISM: ARTIFICIAL SEQUENCE
<220> FEATURE:
<223> OTHER INFORMATION: CHIMERIC SEQUENCE BASED ON A HUMAN SEQUENCE

<400> SEQUENCE: 2

Arg Ser Leu Ala Phe Phe Ile Tyr Val Pro Met Asn Glu Gln Ile Val
1               5                   10                  15

Ile Gly Arg Leu Asp Glu Asp Ile Ile Leu Pro Ser Ser Phe Glu Arg
            20                  25                  30

Gly Ser Glu Val Val Ile His Trp Lys Tyr Gln Asp Ser Tyr Lys Val
            35                  40                  45

His Ser Tyr Tyr Lys Gly Ser Asp His Leu Glu Ser Gln Asp Pro Arg
    50                  55                  60

Tyr Ala Asn Arg Thr Ser Leu Phe Tyr Asn Glu Ile Gln Asn Gly Asn
65                  70                  75                  80

Ala Ser Leu Phe Phe Arg Arg Val Ser Leu Leu Asp Glu Gly Ile Tyr
                85                  90                  95

Thr Cys Tyr Val Gly Thr Ala Ile Gln Val Ile Thr Asn Lys Val Val
            100                 105                 110

Leu Lys Val Gly Val Phe Leu Thr Pro Val Met Lys Tyr Glu Lys Arg
            115                 120                 125

Asn Thr Asn Ser Phe Leu Ile Cys Ser Val Leu Ser Val Tyr Pro Arg
    130                 135                 140

Pro Ile Ile Thr Trp Lys Met Asp Asn Thr Pro Ile Ser Glu Asn Asn
145                 150                 155                 160

Met Glu Glu Thr Gly Ser Leu Asp Ser Phe Ser Ile Asn Ser Pro Leu
                165                 170                 175

Asn Ile Thr Gly Ser Asn Ser Ser Tyr Glu Cys Thr Ile Glu Asn Ser
            180                 185                 190

Leu Leu Lys Gln Thr Trp Thr Gly Arg Trp Thr Met Lys Asp Gly Leu
            195                 200                 205

His Lys Met Gln Ser Glu His Val Ser Leu Ser Cys Gln Pro Val Asn
    210                 215                 220

Asp Tyr Phe Ser Pro Asn Gln Asp Phe Lys Val Thr Trp Ser Arg Met
225                 230                 235                 240

Lys Ser Gly Thr Phe Ser Val Leu Ala Tyr Tyr Leu Ser Ser Ser Gln
                245                 250                 255

Asn Thr Ile Ile Asn Glu Ser Arg Phe Ser Trp Asn Lys Glu Leu Ile
            260                 265                 270
```

-continued

```
Asn Gln Ser Asp Phe Ser Met Asn Leu Met Asp Leu Asn Leu Ser Asp
        275                 280                 285

Ser Gly Glu Tyr Leu Cys Asn Ile Ser Ser Asp Glu Tyr Thr Leu Leu
        290                 295                 300

Thr Ile His Thr Val His Val Glu Pro Ser Gln Glu Thr Ala Ser Gly
305                 310                 315                 320

Gly Arg Ser Lys Thr Ser Gly Ser Glu Pro Lys Ser Cys Asp Lys Thr
                325                 330                 335

His Thr Cys Pro Pro Cys Pro Ala Pro Glu Leu Leu Gly Gly Pro Ser
            340                 345                 350

Val Phe Leu Phe Pro Pro Lys Pro Lys Asp Thr Leu Met Ile Ser Arg
        355                 360                 365

Thr Pro Glu Val Thr Cys Val Val Val Asp Val Ser His Glu Asp Pro
370                 375                 380

Glu Val Lys Phe Asn Trp Tyr Val Asp Gly Val Glu Val His Asn Ala
385                 390                 395                 400

Lys Thr Lys Pro Arg Glu Glu Gln Tyr Asn Ser Thr Tyr Arg Val Val
                405                 410                 415

Ser Val Leu Thr Val Leu His Gln Asp Trp Leu Asn Gly Lys Glu Tyr
            420                 425                 430

Lys Cys Lys Val Ser Asn Lys Ala Leu Pro Ala Pro Ile Glu Lys Thr
        435                 440                 445

Ile Ser Lys Ala Lys Gly Gln Pro Arg Glu Pro Gln Val Tyr Thr Leu
    450                 455                 460

Pro Pro Ser Arg Glu Glu Met Thr Lys Asn Gln Val Ser Leu Thr Cys
465                 470                 475                 480

Leu Val Lys Gly Phe Tyr Pro Ser Asp Ile Ala Val Glu Trp Glu Ser
                485                 490                 495

Asn Gly Gln Pro Glu Asn Asn Tyr Lys Thr Thr Pro Pro Val Leu Asp
            500                 505                 510

Ser Asp Gly Ser Phe Phe Leu Tyr Ser Lys Leu Thr Val Asp Lys Ser
        515                 520                 525

Arg Trp Gln Gln Gly Asn Val Phe Ser Cys Ser Val Met His Glu Ala
    530                 535                 540

Leu His Asn His Tyr Thr Gln Lys Ser Leu Ser Leu Ser Pro Gly Lys
545                 550                 555                 560

<210> SEQ ID NO 3
<211> LENGTH: 1734
<212> TYPE: DNA
<213> ORGANISM: ARTIFICIAL SEQUENCE
<220> FEATURE:
<223> OTHER INFORMATION: NUCLEIC ACID ENCODING CHIMERIC SEQUENCE BASED
      ON HUMAN SEQUENCE

<400> SEQUENCE: 3
atgaagttat gcatattact ggccgtcgtg gcctttgttg cctctcgct cgggagatct      60 ttggctttct tcatttatgt tcctatgaat gaacaaatcg tcattggaag acttgatgaa    120
gatataattc tccttcttc atttgagagg ggatccgaag tcgtaataca ctggaagtat    180
caagatagct ataaggttca tagttactac aaaggcagtg accatttgga aagccaagat    240
cccagatatg caaacaggac atcccttttc tataatgaga ttcaaaatgg gaatgcgtca    300
ctatttttca gaagagtaag ccttctggac gaaggaattt acacctgcta tgtaggaaca    360
gcaattcaag tgattacaaa caaagtggtg ctaaaggtgg agttttttct cacacccgtg    420
```

```
atgaagtatg aaaagaggaa cacaaacagc ttcttaatat gcagcgtgtt aagtgtttat    480
cctcgtccaa ttatcacgtg gaaaatggac aacacaccta tctctgaaaa caacatggaa    540
gaaacagggt ctttggattc tttttctatt aacagcccac tgaatattac aggatcaaat    600
tcatcttatg aatgtacaat tgaaaattca ctgctgaagc aaacatggac agggcgctgg    660
acgatgaaag atggccttca taaaatgcaa agtgaacacg tttcactctc atgtcaacct    720
gtaaatgatt atttttcacc aaaccaagac ttcaaagtta cttggtccag aatgaaaagt    780
gggactttct ctgtcctggc ttactatctg agctcctcac aaaatacaat tatcaatgaa    840
tcccgattct catggaacaa agagctgata accagagtg acttctctat gaatttgatg    900
gatcttaatc tttcagacag tggggaatat ttatgcaata tttcttcgga tgaatatact    960
ttacttacca tccacacagt gcatgtagaa ccgagccaag aaacagcttc cggcggccgc   1020
tctaaaacta gtggatccga gcccaaatct tgtgacaaaa ctcacacatg cccaccgtgc   1080
ccagcacctg aactcctggg gggaccgtca gtcttcctct tccccccaaa acccaaggac   1140
accctcatga tctcccggac ccctgaggtc acatgcgtgg tggtggacgt gagccacgaa   1200
gaccctgagg tcaagttcaa ctggtacgtg gacggcgtgg aggtgcataa tgccaagaca   1260
aagccgcggg aggagcagta caacagcacg taccgtgtgg tcagcgtcct caccgtcctg   1320
caccaggact ggctgaatgg caaggagtac aagtgcaagg tctccaacaa agccctccca   1380
gcccccatcg agaaaaccat ctccaaagcc aaagggcagc cccgagaacc acaggtgtac   1440
accctgcccc catcccggga ggagatgacc aagaaccagg tcagcctgac ctgcctggtc   1500
aaaggcttct atcccagcga catcgccgtg gagtgggaga gcaatgggca gccggagaac   1560
aactacaaga ccacgcctcc cgtgctggac tccgacggct ccttcttcct ctatagcaag   1620
ctcaccgtgg acaagagcag gtggcagcag gggaacgtct tctcatgctc cgtgatgcat   1680
gaggctctgc acaaccacta cacgcagaag agcctctccc tgtctccggg taaa         1734
```

<210> SEQ ID NO 4
<211> LENGTH: 11
<212> TYPE: PRT
<213> ORGANISM: HUMAN

<400> SEQUENCE: 4

Thr Thr Gly Val Tyr Val Lys Met Pro Pro Thr
1               5                   10